United States Patent [19]

Ullrich et al.

[11] Patent Number: 5,589,375
[45] Date of Patent: Dec. 31, 1996

[54] PTP 1D: A NOVEL PROTEIN TYROSINE PHOSPHATASE

[75] Inventors: Axel Ullrich, Martinsried bei Muchen; Wolfgang Vogel, Germering, both of Germany

[73] Assignee: Max-Planck-Gesellschaft Zur Forderung Der Wissenschaften E. V., Gottingen, Germany

[21] Appl. No.: 18,129

[22] Filed: Feb. 16, 1993

Related U.S. Application Data

[63] Continuation-in-part of Ser. No. 956,315, Oct. 6, 1992, abandoned.

[51] Int. Cl.$^6$ .............................. C12N 5/06; C07H 21/04
[52] U.S. Cl. ..................... 435/240.2; 435/172.3; 435/320.1; 435/252.3; 435/252.33; 435/4; 435/195; 935/14; 935/20; 935/24; 935/32; 935/70; 935/71; 935/72; 935/73; 536/23.2; 536/23.1
[58] Field of Search ................... 536/23.2, 23.1; 435/194, 195, 320.1, 91.1, 91.2, 240.2, 252.3, 252.33, 172.3; 930/240; 935/14, 29, 24, 32, 70, 71, 72, 73

[56] References Cited

U.S. PATENT DOCUMENTS 4,675,285  6/1987  Clark et al. .................. 435/6

FOREIGN PATENT DOCUMENTS 9201050  1/1992  WIPO.

OTHER PUBLICATIONS

Freeman et al. 1992, Proc. Natl. Acad. Sci., USA., 89, 11239–11243.
Mathews et al. 1992. Mol. Cell. Biol. 12, 2396–2405.
Plutzky et al. 1992. Proc. Natl. Acad. Sci. USA 89, 1123–1127.
Yi, et al 1992. Mol. Cell. Biol. 12, 836–846.
Gu et al. 1991 Proc. Natl Acad Sci. USA. 88, 5867–5871.
Lombroso et al 1991 Proc. Natl. Acad. Sci USA 88, 7242–7246.
Shen et al. 1991 Nature 352, 736–739.
Yang et al. 1991. Proc. Natl Acad Sci USA 88, 5949–5953.
Chernoff et al. 1990 Proc. Natl. Acad. Sci. USA. 87, 2735–2739.
Guan et al, 1990. Proc. Natl. Acad. Sci. USA. 87, 1501–1505.
Charbonneau et al. 1989. Proc. Natl Acad Sci USA 86, 5252–5256.
Cool et al. 1989. Proc. Natl Acad Sci USA 86, 5257–5261.
Pallen et al. 1988 Ann. N.Y. Acad Sci. 551, 299–308.
Tonks et al. 1988 J. Biol. Chem. 263, 6722–6730.
Gebbink et al. 1991. FEBS Lett. 290, 123–130.
Jirik et al. 1990 FEBS Lett. 273, 239–242.
Kaplan et al. 1990. Proc. Natl Acad Sci USA 87, 7000–7004.
Krueger et al. 1990 EMBO J. 9, 3241–3252.
Mathews et al. 1990 Proc. Natl. Acad. Sci USA 87, 4444–4448.
Mustelin et al. 1989 Proc. Natl. Acad Sci USA 86, 6302–6306.
Streuli et al. 1988. J. Exp. Med. 168, 1523–1530.
Ralph et al. 1987, EMBO. J. 6, 1251–1257.
Perkins et al. 1992 Cell. 70, 225–236.
Harihan et al. 1991 Proc. Natl. Acad. Sci. USA. 88, 11266–11270.
Streuli et al. 1989 Proc. Natl. Acad Sci. USA. 86, 8698–8702.
Sprenger et al. 1989. Nature 338, 478–483.
Russell et al. 1992 F.E.B.S. 304, 15–20.
Zheng et al. 1992 Nature 359, 336–339.
Stover et al. 1991. Proc. Natl. Acad. Sci. USA 88, 7704–7707.
Margolis et al. 1989 Cell 57, 1101–1107.
Morla et al. 1989. Cell 58, 193–203.
Charbonneau et al, 1992. Annu. Rev. Cell Biol. 8, 463–493.
Pot et al. 1992 Biochim. Biophys. Acta. 1136, 35–43.
Fischer et al. Scierre 253, 401–406.
Koch et al. 1991 Science 252, 668–674.
Hunter, T. 1989. Cell 58, 1013–1016.
Hunter, T. 1987. Cell, 49, 1–4.
Watson, J. D. 1987, in:*Molecular Biology of The Gene.*, 3rd Edition. Benjamin/Cummings Publ. Co., Inc. Menlo Park, CA 94025. p. 313.
*Hackh's Chemical Dictionary*, 1969. (Grant, J., ed.) McGrawHill Book Co., NY, p. 236.
Vogel et al. 1993. Science 259, 1611–1614.
Baker, et al., 1982, in: *The Study of Biology.* Fourth edition. Addison–Wooley Publ. Co., Reading, MA. p. 9.
Co et al, 1992. Biophys J. 61 (2 part 2), A337, abstract 1940.
Day, R. A. 1983. *How to Write and Publish a scientific Paper.* Second Edition. IS1 Press. Philadelphia, PA pp. 15–19.
Zhang et al. 1991 Biochem. Biophys. Res. Commun 178, 1291–1297.

*Primary Examiner*—Christopher S. Low
*Attorney, Agent, or Firm*—Pennie & Edmonds

[57] ABSTRACT

A novel protein tyrosine phosphatase is the protein designated PTP 1D. The PTP 1D protein may be produced by recombinant means, for example using a nucleic acid construct encoding the protein as provided herein. Also disclosed is an antibody specific for an epitope of PTP 1D, protein. Methods for identifying compounds which bind to a PTP 1D protein and inhibit or stimulate its enzymatic activity, pharmaceutical compositions comprising PTP 1D, and methods for treating a disease associated with PTP 1D protein using such compositions, are provided.

10 Claims, 13 Drawing Sheets

```
aatatcatcatgcctgaatttgaaaccaagtgcaacaattcaaagcccaaaaagagttac
------+---------+---------+---------+---------+---------+
ttatagtagtacggacttaaactttggttcacgttgttaagtttcgggttttttctcaatg
```

N  I  I  M  P  E  F  E  T  K  C  N  N  S  K  P  K  K  S  Y

```
attgccacacaaggctgcctgcaaaacacggtgaatgacttttggcggatggtgttccaa
------+---------+---------+---------+---------+---------+
taacggtgtgttccgacggacgttttgtgccacttactgaaaaccgcctaccacaaggtt
```

I  A  T  Q  G  C  L  Q  N  T  V  N  D  F  W  R  M  V  F  Q

```
gaaaactcccgagtgattgtcatgacaacgaaagaagtggagagaggaaagagtaaa
------+---------+---------+---------+---------+-------
cttttgagggctcactaacagtactgttgctttcttcacctctctcctttctcattt
```

```
GGCACGAGCGGCTGGCTCTGCCCCGCGTCCGGTCCCGAGCGGGCCTCCCTCGGGCCAGCCCGATGTGACCGAGCCCAGCGGAGCCTGAGCA      90

AGGAGCGGGTCCGTCGCGGAGCCGGAGGGCGGGAGGAACATGACATCGCGGAGATGGTTTCACCCAAATATCACTGGTGTGGAGGCAGAA     180
                                      M  T  S  R  R  W  F  H  P  N  I  T  G  V  E  A  E      17

AACCTACTGTTGACAAGAGGAGTTGATGGCAGTTTTTTGGCAAGGCCTAGTAAAAGTAACCCTGGAGACTTCACACTTTCCGTTAGAAGA     270
 N  L  L  L  T  R  G  V  D  G  S  F  L  A  R  P  S  K  S  N  P  G  D  F  T  L  S  V  R  R      47

AATGGAGCTGTCACCCACATCAAGATTCAGAACACTGGTGATTACTATGACCTGTATGGACCCGAGAAATTTGCCACTTTGGCTGAGTTG     360
 N  G  A  V  T  H  I  K  I  Q  N  T  G  D  Y  Y  D  L  Y  G  G  E  K  F  A  T  L  A  E  L      77

GTCCAGTATTACATGGAACATCACGGGCAATTAAAAGAGAAGAATCGAGATGTCATTGAGCTTAAATATCCTCTGAACTGTGCAGATCCT     450
 V  Q  Y  Y  M  E  H  H  G  Q  L  K  E  K  N  G  D  V  I  E  L  K  Y  P  L  N  C  A  D  P     107

ACCTCTGAAAGGTGGTTTCATGGACATCTCTCTGGGAAAGAAGCAGAGAAATTATTAACTGAAAAAGGAAAACATGGTAGTTTTCTTGTA     540
 T  S  E  R  W  F  H  G  H  L  S  G  K  E  A  E  K  L  L  T  E  K  G  K  H  G  S  F  L  V     137

CGAGAGAGCCAGAGCCACCCTGGAGATTTTGTTCTTTCTGTGCGCACTGGTGATGACAAAGGGGAGAGCAATGACGGCAAGTCTAAAGTG     630
 R  E  S  Q  S  H  P  G  D  F  V  L  S  V  R  T  G  D  D  K  G  E  S  N  D  G  K  S  K  V     167

ACCCATGTTATGATTCGCTGTCAGGAACTGAAATACGACGTTGGTGGAGGAGAACGGTTTGATTCTTTGACAGATCTTGTGGAACATTAT     720
 T  H  V  M  I  R  C  Q  E  L  K  Y  D  V  G  G  G  E  R  F  D  S  L  T  D  L  V  E  H  Y     197

AAGAAGAATCCTATGGTGGAAACATTGGGTACAGTACTACAACTCAAGCAGCCCCAATTCTCGACTCGTATAAATGCTGCTGAAATAGAA     810
 K  K  N  P  M  V  E  T  L  G  T  V  L  Q  L  K  Q  P  Q  F  S  T  R  I  N  A  A  E  I  E     227

AGCAGAGTTCGAGAACTAAGCAAATTAGCTGAGACCACAGATAAAGTCAAACAAGGCTTTTGGGAAGAATTTGAGACACTACAACAACAG     900
 S  R  V  R  E  L  S  K  L  A  E  T  T  D  K  V  K  Q  G  F  W  E  E  F  E  T  L  Q  Q  Q     257

GAGTGCAAACTTCTCTACAGCCGAAAAGAGGGTCAAAGGCAAGAAAACAAAAACAAAAATAGATATAAAAACATCCTGCCCTTTGATCAT     990
 E  C  K  L  L  Y  S  R  K  E  G  Q  R  Q  E  N  K  N  K  N  R  Y  K  N  I  L  P  F  D  H     287

ACCAGGGTTGTCCTCACGATCTGTGATCCCAATGAGCCTGTTTCAGATTACATCAATGCAAATATCATCATGCCTGAATTTGAAACCAAG    1080
 T  R  V  V  L  T  I  C  D  P  N  E  P  V  S  D  Y  I  N  A  N  I  I  M  P  E  F  E  T  K     317

TGCAACAATTCAAAGCCCAAAAAGAGTTACATTGCCACACAAGGCTGCCTGCAAAACACGGTGAATGACTTTTGGCGGATGGTGTTCCAA    1170
 C  N  N  S  K  P  K  K  S  Y  I  A  T  Q  G  C  L  Q  N  T  V  N  D  F  W  R  M  V  F  Q     347
```

FIG.2A

```
GAAAACTCCCGAGTGATTGTCATGACAACGAAAGAAGTGGAGAGAGGAAAGAGTAAATGTGCTCAATACTGGCCTGATGAGTATGCTCTA  1260
 E  N  S  R  V  I  V  M  T  T  K  E  V  E  R  G  K  S  K  C  A  Q  Y  W  P  D  E  Y  A  L    377

AAAGAATATGGCGTCATGCGTGTTAGGAACGTCAAAGAAAGCGCCGCTCATGACTATACGCTAAGAGAACTTAAACTTTCAAAGGTTCGA  1350
 K  E  Y  G  V  M  R  V  R  N  V  K  E  S  A  A  H  D  Y  T  L  R  E  L  K  L  S  K  V  G    407

CAAGGGAATACGGAGAGAACCGTCTGGCAATACCACTTTCGGACCTGGCCCGACCACGGCGTGCCCAGCGACCCTGGGGGCGTGCTGGAC  1440
 Q  G  N  T  E  R  T  V  W  Q  Y  H  F  R  T  W  P  D  H  G  V  P  S  D  P  G  G  V  L  D    437

TTCCTGGAGGAGGTGCACCATAAGCAGGAGAGCATCATGGATGCAGGGCCGTCGTGGTGCACTGCAGTGCTGGAATTGGCCGGACAGGG  1530
 F  L  E  E  V  H  H  K  Q  E  S  I  M  D  A  G  P  V  V  H  C  S  A  G  I  G  R  T  G      467

ACGTTCATTGTGATTGATATTCTTATTGACATCATCAGAGAGAAACGTGTTGACTGCGATATTGACGTTCCCAAAACCATCCAGATGGTG  1620
 T  F  I  V  I  D  I  L  I  D  I  I  R  E  K  G  V  D  C  D  I  D  V  P  K  T  I  Q  M  V    497

CGGTCTCAGAGGTCAGGGATGGTCCAGACAGAAGCACAGTACCGATTTATCTATATGGCCGGTCCAGCATTATATTGAAACACTACAGCGC  1710
 R  S  Q  R  S  G  M  V  Q  T  E  A  Q  Y  R  F  I  Y  M  A  V  Q  H  Y  I  E  T  L  Q  R    527

AGGATTGAAGAAGAGCAGAAAAGCAAGAGGAAAGGGCACGAATATACAAATATTAAGTATTCTCTAGCGGACCAGACGAGTGGAGATCAG  1800
 R  I  E  E  E  Q  K  S  K  R  K  G  H  E  Y  T  N  I  K  Y  S  L  A  D  Q  T  S  G  D  Q    557

AGCCCTCTCCCGCCTTGTACTCCTTCGCCACCCTGTGCAGAAATGAGAGAAGACAGTGCTAGAGTCTATGAAAACGTGGGCCTGATGCAA  1890
 S  P  L  P  P  C  T  P  S  P  P  C  A  E  M  R  E  D  S  A  R  V  Y  E  N  V  G  L  M  Q    587

CAGCAGAAAAGTTTCAGATGAGAAAACCTGCCAAAACTTCAGCACAGAAATAGATGTGGACTTTCACCTCTCCCTAAAAAGATCAGGACC  1980
 Q  Q  K  S  F  R

AGACGCAAGAAAGTTTATGTGAAGTCTGAATTTGGATTTGGAAGGCTTGCAATGTGGTTGACTACCTTTTGATAAGCAAAATTTGAAACC  2070
ATTTAAAGACCACTGTATTTTAACTCAACAATACCTGCTTCCCAATTACTCATTTCCTCAGATAAGAAGAAATCATCTCTACAATGTAGA  2160
CAACATTATATTTTATAGAATTTGTTTGAAATTGAGGAAGCAGTTAAATTGTGCGCTGTATTTTGCAGATTATGGGGATTCAAATTCTAG  2250
TAATAGGCTTTTTTATTTTTATTTTTATACCCTTAACCAGTTTAATTTTTTTTTTTCCTCATTGTTGGGGATGATGAGAAGAAATGATTT  2340
GGGAAAATTAAGTAACAACGACCTAGAAAAGTGAGAACAATCTCATTTACCATCATGTATCCAGTAGTGGATAATTCATTTTGATGGCTT  2430
CTATTTTGCCCAAATGAGAATTAAGCCAGTGCCTGAGACTGTCAGAAGTTGACCTTTGCACTGGCATTAAAGAGTCATAGAAAAAGAATC  2520
ATGGATATTTATGAATTAAGGTAAGAGGTGTGGCTTTTTTTTTTTTCTTTTTTCCAGCCCGTTGACCAATTATAGTTCGGCTCTTGACTGA  2610
GAAGTTGTGGTGGAAACGTTTGCCATATTTTCTTTGCATTTGAATAATTGTCTTGTACTTAGAAAAAAGGCGTCTATGAATGACCAGTGT  2700
TTTTCGTCGCCCAAATGTTGCTGACAAACTTATCCCAAAACTTTAGTGGCTTAAAAAAAACCTGCCCCCAACTGTTAGTCAATTGAGCTGGG  2790
```

FIG.2B

```
GGCACGAGCCGCTGGCTCTGCCCGCGTCCCGTCCCGAGCCGGGCCTCCCTCGGGCCAGCCCCGATGTGACCGAGCCCAGCGGAGCCTGAGCA   90

AGGAGCGGGTCCGTCGCCGAGCCGGAGGCCGGAGGAACATGACATCGCGGAGATGGTTTCACCCAAATATCACTGGTGTGGAGGCAGAA   180
                                    M T S R R W F H P N I T G V E A E          17

AACCTACTGTTGACAAGAGGAGTTGATGGCAGTTTTTTGGCAAGGCCTAGTAAAAGTAACCCTGGAGACTTCACACTTTCCGTTAGAAGA   270    SH2
N L L L T R G V D G S F L A R P S K S N P G D F T L S V R R                      47

AATGGAGCTGTCACCCACATCAAGATTCAGAACACTGGTGATTACTATGACCTGTATGGAGGGGAGAAATTTGCCACTTTGGCTGAGTTG   360
N G A V T H I K I Q N T G D Y Y D L Y G G E K F A T L A E L                      77

GTCCAGTATTACATGGAACATCACGGGCAATTAAAAGAGAAGAATGGAGATGTCATTGAGCTTAAATATCCTCTGAACTGTGCAGATCCT   450
V Q Y Y M E H H G Q L K E K N G D V I E L K Y P L N C A D P                      107

ACCTCTGAAAGGTGGTTTCATGGACATCTCTCTGGGAAAGAAGCAGAGAAATTATTAACTGAAAAAGGAAAACATGGTAGTTTTCTTGTA   540
T S E R W F H G H L S G K E A E K L L T E K G K H G S F L V                      137

CGAGAGAGCCAGAGCCACCCTGGAGATTTTGTTCTTTCTGTGCGCACTGGTGATGACAAAGGGGAGAGCAATGACGGCAAGTCTAAAGTG   630    SH2
R E S Q S H P G D F V L S V R T G D D K G E S N D G K S K V                      167

ACCCATGTTATGATTCGCTGTCAGGAACTGAAATACGACGTTGGTGGAGGAGAACGGTTTGATTCTTTGACAGATCTTGTGGAACATTAT   720
T H V M I R C Q E L K Y D V G G E R F D S L T D L V E H Y                        197

AAGAAGAATCCTATGGTGGAAACATTGGGTACAGTACTACAACTCAAGCAGCCCCTTAACACGACTCGTATAAATGCTGCTGAAATAGAA   810
K K N P M V E T L G T V L Q L K Q P L N T T R I N A A E I E                      227

AGCAGAGTTCGAGAACTAAGCAAATTAGCTGAGACCACAGATAAAGTCAAACAAGGCTTTTGGGAAGAATTTGAGACACTACAACAACAG   900
S R V R E L S K L A E T T D K V K Q G F W E E F E T L Q Q Q                      257

GAGTGCAAACTTCTCTACAGCCGAAAAGAGGGTCAAAGGCAAGAAAACAAAAACAAAAATAGATATAAAAACATCCTGCCCTTTGATCAT   990
E C K L L Y S R K E G Q R Q E N K N K N R Y K N I L P F D H                      287

ACCAGGGTTGTCCTACACGATGGTGATCCCAATGAGCCTGTTTCAGATTACATCAATGCAAATATCATCATGCCTGAATTTGAAACCAAG   1080   PTP
T R V V L H D G D P N E P V S D Y I N A N I I M P E F E T K                      317

TGCAACAATTCAAAGCCCAAAAAGAGTTACATTGCCACACAAGGCTGCCTGCAAAACACGGTGAATGACTTTTGGCGGATGGTGTTCCAA   1170
C N N S K P K K S Y I A T Q G C L Q N T V N D F W R M V F Q                      347
```

FIG. 3A

```
GAAAACTCCCGAGTGATTGTCATGACAACGAAAGAAGTGGAGAGAGGAAAGAGTAAATGTGTCAAATACTGGCCCTGATGAGTATGCTCTA  1260
 E  N  S  R  V  I  V  M  T  T  K  E  V  E  R  G  K  S  K  C  V  K  Y  W  P  D  E  Y  A  L    377  PTP

AAAGAATATGGCGTCATGCGTGTTAGGAACGTCAAAGAAAGCGCCGCTCATGACTATACGCTAAGAGAACTTAAACTTTCAAAGGTTGGA  1350
 K  E  Y  G  V  M  R  V  R  N  V  K  E  S  A  A  H  D  Y  T  L  R  E  L  K  L  S  K  V  G    407

CAAGGGAATACCGAGAGAACGGTCTGCCAATACCACTTTCGGACCTGGCCGGACCACGGCGTGCCCAGCGACCCTGGGGGCCTGCTGGAC  1440
 Q  G  N  T  E  R  T  V  W  Q  Y  H  F  R  T  W  P  D  H  G  V  P  S  D  P  G  G  V  L  D    437

TTCCTGGAGGACGTGCACCATAAGCAGGAGAGCATCATGGATGCAGGGCCCGTCGTGGTGCACTGCAGTGCTGGAATTGGCCGGACAGGG  1530
 F  L  E  E  V  H  H  K  Q  E  S  I  M  D  A  G  P  V  V  V  H  C  S  A  G  I  G  R  T  G    467

ACGTTCATTGTGATTGATATTCTTATTGACATCATCAGAGAGAAAGGTGTTGACTGCGATATTGACGTTCCCAAAACCATCCAGATGGTG  1620
 T  F  I  V  I  D  I  L  I  D  I  I  R  E  K  G  V  D  C  D  I  D  V  P  K  T  I  Q  M  V    497

CGGTCTCAGAGGTCAGGGATGGTCCAGACAGAAGCACAGTACCGATTTATCTATATGGCGGTCCAGCATTATATTGAAACACTACAGCGC  1710
 R  S  Q  R  S  G  M  V  Q  T  E  A  Q  Y  R  F  I  Y  N  A  V  Q  H  Y  I  E  T  L  Q  R    527

AGGATTGAAGAAGAGCAGAAAAGCAAGAGGAAAGGCCACGAATATACAAATATTAAGTATTCTCTAGCGGACCAGACGAGTGGAGATCAG  1800
 R  I  E  E  E  Q  K  S  K  R  K  G  H  E  Y  T  N  I  K  Y  S  L  A  D  Q  T  S  G  D  Q    557

AGCCCTCTCCCGCCTTGTACTCCAACGCCACCCTGTGCAGAAATGAGAGAAGACAGTGCTAGAGTCTATGAAAACGTGGGCCTGATGCAA  1890
 S  P  L  P  P  C  T  P  T  P  P  C  A  E  M  R  E  D  S  A  R  V  Y  E  N  V  G  L  M  Q    587

CAGCAGAAAAGTTTCAGATGAGAAAACCTGCCAAAACTTCAGCACAGAAATAGATGTGGACTTTCACCTCTCCCTAAAAAGATCAGGACC  1980
 Q  Q  K  S  F  R  *                                                                          593

---//---GCAAAGCTGTATTATCAGAGTAAAAGTGTATTTGTAAACTGTATGGGAACTAAAAATTAGGAATAAAACCATTTTCTTATAn  6800
```

PTP 1D: A NOVEL PROTEIN TYROSINE PHOSPHATASE

1. CROSS REFERENCE TO RELATED APPLICATION

This application is a continuation-in-part of U.S. application Ser. No. 07/956,315, filed Oct. 6, 1992, now abandoned which is incorporated herein by reference in its entirety.

2. BACKGROUND OF THE INVENTION

2.1. Field of the Invention

This invention, in the fields of biochemistry and cell and molecular biology, relates to a novel protein tyrosine phosphatase (PTP) termed PTP 1D. Included is the PTP 1D protein, nucleic acid constructs coding therefor, recombinant expression vectors comprising the nucleic acid construct, cells containing or expressing the recombinant expression vectors, methods for producing and identifying PTP 1D protein and DNA constructs, antibodies specific for PTP 1D protein and glycoprotein, and methods for screening compounds capable of binding to and inhibiting or stimulating protein tyrosine phosphatase enzymatic activity of PTP 1D.

2.2. Description of the Background Art

2.2.1. Introduction

Phosphorylation of proteins is a fundamental mechanism for regulating diverse cellular processes. While the majority of protein phosphorylation occurs at serine and threonine residues, phosphorylation at tyrosine residues has attracted much interest since the discovery that many oncogene products and growth factor receptors possess intrinsic protein tyrosine kinase (PTKase or PTK) activity. The importance of protein tyrosine phosphorylation in growth factor signal transduction, cell cycle progression and neoplastic transformation is now well established (Hunter et al., *Ann. Rev. Biochem.* 54:987–930 (1985); Ullrich et al., *Cell* 61:203–212 (1990); Nurse, *Nature* 344:503–508 (1990); Cantley et al., *Cell* 64:281–302 (1991)).

The phosphorylation of protein tyrosine residues is a dynamic process with competing phosphorylation and dephosphorylation reactions. These processes are regulated by the reciprocal actions of PTKs, which catalyze tyrosine phosphorylation, and protein tyrosine phosphatases (PTPases or PTPs), which specifically dephosphorylate tyrosine residues of phosphorylated proteins. The net level of tyrosine phosphorylation of intracellular proteins is thus determined by the balance of PTK and PTP enzymatic activities. (Hunter, T., *Cell* 58:1013–1016 (1989)).

2.2.2. Protein Tyrosine Kinases

PTKs comprise a large family of proteins, including many growth factor receptors and potential oncogenes which share ancestry with, but nevertheless differ from, serine/threonine-specific protein kinases (Hanks et al., *Science* 241:42–52 (1988)). Many PTKs have been linked to initial signals in the induction of the cell cycle (Weaver et al., *Mol. Cell. Biol.* 11:4415–4422 (1991)).

Most of our current understanding of mechanisms underlying changes in PTKs comes from receptor-type PTKs (RPTKs) having a transmembrane topology. The binding of a specific ligand to the extracellular domain of an RPTK is thought to induce oligomerization, increasing the enzymatic (kinase) activity and activation of the signal transduction pathways (Ullrich et al., supra). Dysregulation of kinase activity through mutation or overexpression is a well-established mechanism underlying cell transformation (Hunter et al., 1985, supra; Ullrich et al., supra).

2.2.3. Protein Tyrosine Phosphatases

The protein phosphatases comprise at least two separate and distinct families (Hunter, T., 1989, supra): protein serine/threonine phosphatases and protein tyrosine phosphatases (PTPs). The PTPs are themselves a family, containing at least two subgroups. The first subgroup comprises low molecular weight, intracellular enzymes that contain a single conserved catalytic phosphatase domain. Members of this subgroup include:

(1) placental PTP 1B (Charbonneau et al., *Proc. Natl. Acad. Sci. USA* 86:5252–5256 (1989); Chernoff et al., *Proc. Natl. Acad. Sci. USA* 87:2735–2789 (1989));

(2) T-cell PTP (Cool et al. *Proc. Natl. Acad. Sci. USA* 86:5257–5261 (1989));

(3) rat brain PTP (Guan et al., *Proc. Natl. Acad. Sci. USA* 87:1501–1502 (1990));

(4) neuronal phosphatase (STEP) (Lombroso et al., *Proc. Natl. Acad. Sci. USA* 88:7242–7246 (1991)); and (5) cytoplasmic phosphatases that contain a region of homology to cytoskeletal proteins (Gu et al., *Proc. Natl. Acad. Sci. USA* 88:5867–57871 (1991); Yang et al., *Proc. Natl. Acad. Sci. USA* 88:5949–5953 (1991)).

Since the first PTP was purified, sequenced and cloned, additional potential PTPs have been identified at a rapid pace, and the number continues to grow steadily. The large number of known members of the PTP family suggests that there may be specificity in PTP-RPTK interactions. A cDNA encoding a novel PTP designated PTP 1C was cloned from several sources (Shen, S.-H. et al., *Nature* 352:736–739 (1991); Plutzky, J. et al., *Proc. Natl. Acad. Sci. USA* 1123-(1992); Yi, T., et al., *Mol. Cell. Biol.* 12:836–846 (1992); Matthews, R. J. et al., *Molec. Cell. Biol.* 2396-(1992)). The PTP 1C protein has a single catalytic domain and a pair of N-terminally located src-homology regions, termed SH2, suggesting that PTK activity could be directly regulated by SH2 domain-mediated interaction with a PTP.

The second PTP subgroup includes the high molecular weight, receptor-linked PTPs, termed RPTPs. RPTPs consist of (a) an intracellular catalytic region, (b) a single transmembrane segment, and (c) a putative ligand-binding extracellular domain (Gebbink, M. F. et al., *FEBS Lett.* 290:123–130 (1991)). The structures and sizes of the putative "extracellular receptor" domains of various RPTPs are diverse, whereas the intracellular catalytic domains are highly conserved. All RPTPs have two tandemly duplicated catalytic phosphatase homology domains, with the exception of HPTPO, which has only one. (Tsai et al., *J. Biol. Chem.* 266:10534–10543 (1991)).

One RPTP, originally named the leukocyte common antigen (LCA) (Ralph, S. J., *EMBO J.* 6:1251–1257 (1987)), has been known by other names, including T200 (Trowbridge et al., *Eur. J. Immunol.* 6:557–562 (1962)), B220 for the B cell form (Coffman et al., *Nature* 289:681–683 (1981)), the mouse allotypic marker Ly-5 (Komuro et al., *Immunogenetics* 1:452–456 (1975)), and more recently, CD45 (Cobbold et al., *Leucocyte Typing III*, McMichael et al., eds., pp. 788–803, 1987). The LCA molecules comprise a family of high molecular weight glycoproteins expressed on the surface of all leukocytes and their hemopoietic progenitors (Thomas, *Ann. Rev. Immunol.* 7:339–369 (1989)), and have remarkable sequence homology between animal species (Charbonneau et al., *Proc. Natl. Acad. Sci. USA* 85:7182–7186 (1988)). CD45 is thought to play a critical role in T cell activation. (For review, see: Weiss A., *Ann. Rev. Genet.* 25:487–510 (1991).) Thus, mutagenized T cell clones which did not express CD45 were functionally impaired in responding to stimulation via the T cell receptor (Weaver et al., 1991, supra). CD45 PTP activity played a role in the activation of pp56$^{1ck}$, a lymphocyte-specific PTK (Mustelin et al., *Proc. Natl. Acad. Sci. USA* 86:6302–6306 (1989); Ostergaard et al., *Proc. Natl. Acad. Sci. USA* 86:8959–8963 (1989)). These findings led to the hypothesis that T cell activation involved the phosphatase enzyme activating pp56$^{1ck}$ by dephosphorylation of a C-terminal tyrosine residue.

Another RPTP, the leukocyte common antigen related molecule, LAR (Streuli et al., *J. Exp. Med.* 168:1523–1530 (1988)), was initially identified as an LCA homologue in which the intracellular catalytic region had two catalytic phosphatase homology domains (domains I and II). However, only domain I appeared to have phosphatase activity (Streuli et al., *EMBO J.* 9(8):2399–2407 (1990)). Chemically-induced LAR mutants (tyr$^{1379}$→phe) were temperature-sensitive (Tsai et al., *J. Biol. Chem.* 266(16):10534–10543 (1991)).

A murine RPTP, designated mRPTPμ, has an extracellular domain sharing structural motifs with LAR (Gebbink et al., supra). The human homologue of RPTPμ was cloned, and the gene was localized to human chromosome 18. Two Drosophila PTPs, termed DLAR and DPTP were predicted based on the sequences of cDNA clones (Streuli et al., *Proc. Natl. Acad. Sci. USA* 86:8698–8702 (1989)). cDNA encoding another Drosophila RPTP, DPTP 99A, has also been cloned and characterized (Hariharan et al., *Proc. Natl. Acad. Sci. USA* 88:11266–11270 (1991)).

Other examples of RPTPs include RPTP-α, β, γ, and ζ (Krueger et al., *EMBO J.* 9:3241–3252 (1990), Sap et al., *Proc. Natl. Acad. Sci. USA* 87::6112–6116 (1990), Kaplan et al., *Proc. Natl. Acad. Sci. USA* 87:7000–7004 (1990), Jirik et al., *FEBS Lett.* 273:239–242 (1990), Mathews et al., *Proc. Natl. Acad. Sci. USA* 87:4444–4448 (1990), Ohagi et al., *Nucl. Acids Res.* 18:7159 (1990)). PCT Publication WO92/01050 discloses human RPTP-α, β and γ, and the nature of the structural homologies found among the conserved domains of these three RPTPs and other members of this protein family. An intracellular domain of murine RPTP-α is homologous to the catalytic domains of other PTPs. The 142 amino acid extracellular domain (including signal peptide) of RPTP-α has a high serine and threonine content (32%) and 8 potential N-glycosylation sites. cDNA clones encoding RPTP-α have been produced and expressed in eukaryotic hosts. Natural expression of RPTP-α protein in various cells and tissues was detected with a polyclonal antibody to RPTP-α, produced by immunization with a synthetic RPTP-α peptide. This antibody detected a 130 kDa protein in cells transfected with a cDNA clone encoding a portion of RPTP-α.

Another RPTP, HEPTP, was discovered by screening of a hepatoblastoma cell line (HepG2) cDNA library with a probe encoding the two PTP domains of LCA (Jirik et al., *FASEB J.* 4A:2082, Abstr 2253 (1990)). The HEPTP gene appeared to be expressed in a variety of human and murine cell lines and tissues.

The PTP D subfamily of PTPs was disclosed in a commonly assigned, related U.S. patent application Ser. No. 07/923,740, filed Aug. 5, 1992, the entire contents of which are hereby incorporated by reference.

Conserved amino acid sequences in the catalytic domains of known PTPs have been identified (Krueger et al., *EMBO J.* 9:324–3252 (1990); Yi et al., *Mol. Cell. Biol.* 12:836–846 (1992), both of which references are incorporated herein by reference in their entirety). These amino acid sequences are designated "consensus sequences" herein. Yi et al. aligned the catalytic phosphatase domain sequences of LCA, PTP1B, TCPTP, LAR, DLAR, HPTPα, HPTPβ and HPTPγ, identifying the following "consensus sequences" (See: Yi et al., supra, FIG. 2(A), lines 1–2):

1. D Y I N A S/N [SEQ. ID NO: 1]
2. K C X X Y W P [SEQ. ID NO: 2]

Krueger et al., aligned the catalytic phosphatase domain sequences of PTP1B, TCPTP, LAR, LCA, HPTPα, HPTPβ, HPTPγ, HPTPε and HPTPζ, DLAR and DPTP, identifying the following "consensus sequences" (See: Krueger et al., supra, FIG. 7, lines 1–2):

1. D/N Y I N A S/N [SEQ. ID NO: 3]
2. K C X X Y W P [SEQ. ID NO: 2]

Inclusion of the PTP 1D, csw (corkscrew) and PTP 1C in the sequence comparisons revealed that the conserved sequence QGP is altered in the SH2 domain-containing phosphatases to QGC.

Dephosphorylation of tyrosine residues can, by itself, function as an important cellular regulatory mechanism. Thus, with the src family of tyrosine kinases, dephosphorylation of a C-terminal tyrosine activated the kinase enzymatic activity (Hunter, T., *Cell* 49:1–4 (1987)). Tyrosine dephosphorylation may be an obligatory step in the mitotic activation of the maturation-promoting factor (MPF) kinase (Morla et al., *Cell* 58:193–203 (1989)).

2.2.4. Interactions between Protein Tyrosine Kinases and Phosphatases

Cellular factors involved in signalling include polypeptide substrates which contain the src-homologous regions designated SH2 and SH3, either alone or in combination with an enzymatic activity (Koch, C. A. et al., *Science* 252:668 (1991); Russell, R. B. et al., *FEBS Lett.* 304:15 (1992)). For example, phospholipase Cγ is activated upon interaction with and phosphorylation by the cytoplasmic domain of a RPTK (Margolis, B. et al., *Cell* 57:1101–1107 (1989); Meisenhelder, J. et al., *Cell* 57:1109 (1989); Burgess, W. H. et al., *Mol. Cell. Biol.* 10:4470 (1990); Nishibe, S. et l., *Science* 250:1253 (1990)). While PTPs are thought to be regulators of PTKs, the activation of these crucial components of phosphotyrosine signalling cascades are still not understood (Fischer, E. H. et al., *Science* 253:401 (1991); Pot, D. A. et al., *Biochim. Biophys. Acta* 1136:35 (1992)).

The existence of a large number of PTP family members (described above) suggests that there may be specificity in interactions between particular PTPs and PTKs. The structure of the PTP 1C molecule, discussed above, includes, in addition to a single catalytic domain, a pair of N-terminally-located SH2 regions. The presence of these SH2 regions suggests that PTK activity can be directly regulated by SH2 domain-mediated interaction with a PTP.

The above observations point out the need in the art for understanding the mechanisms that regulate PTP activity. Further analysis of structure-function relationships among PTPs are needed to gain important understanding of the mechanisms of signal transduction, cell cycle progression and cell growth, neoplastic transformation and the fundamental changes in a number of important diseases including cancer and diabetes.

3. SUMMARY OF THE INVENTION

The inventors describe herein the identification, cloning and sequencing of a novel protein tyrosine phosphatase (PTP) designated PTP 1D which differs significantly in structure from most previously reported PTPs, and has 71% sequence similarity with PTP 1C.

Thus, the present invention provides a PTP 1D protein, or a functional derivative thereof, wherein, when the PTP 1D protein is one which occurs in nature, the PTP 1D protein is substantially free of other proteins or glycoproteins with which it is natively associated.

Preferably, the PTP 1D protein comprises an amino acid sequence that has 71% or more identity with the amino acid sequence of PTP 1D shown in FIGS. 2A–2B (SEQ ID NO:3). More preferably, the PTP 1D protein comprises SEQ ID NO:5.

A substantially pure PTP 1D protein, may be produced by biochemical purification, or may be prepared by chemical means or by recombinant means in a prokaryotic or eukaryotic host, and is provided substantially free of other proteins with which it Is natively associated and/or has modified amino acids.

The functional derivative of the PTP 1D protein, includes a fragment, a protein or peptide with additional or substituted amino acids, a PTP 1D protein having any combination of deleted, additional, or substituted amino acids, such that the PTP 1D protein possesses the desired biological activity.

Also provided herein is a recombinant nucleic acid construct comprising a nucleotide sequence encoding a PTP 1D protein, or encoding a functional derivative thereof. Such nucleic acid construct may be a cDNA or a genomic DNA molecule. It is preferably an expression vehicle such as a plasmid. In a preferred embodiment, the nucleic acid construct encodes PTP 1D and comprises the nucleotide sequence shown in FIGS. 2A–2B [SEQ ID NO:4]

Also provided is an isolated and purified nucleic acid construct comprising a nucleotide sequence encoding the PTP 1D protein. Preferably, the nucleotide sequence is SEQ. ID NO:4.

The present invention includes as a prokaryotic and a eukaryotic host cell transformed or transfected with, or otherwise containing, the above expression vehicle or plasmid.

Also provided is a method for preparing a PTP 1D protein, comprising:
(a) culturing a host cell capable of expressing the PTP 1D protein under culturing conditions,
(b) expressing the PTP 1D protein; and
(c) recovering the PTP 1D protein from the culture.

The present invention is also directed to an antibody, including a polyclonal, monoclonal, or chimeric antibody, specific for an epitope of a PTP 1D protein.

The invention is further directed to a method for detecting the presence of or measuring the quantity of PTP 1D in a cell, the method comprising:
(a) contacting the cell or an extract thereof with an antibody specific for an epitope of PTP 1D protein; and
(b) detecting the binding of the antibody to the cell or extract thereof, or measuring the quantity of antibody bound, thereby determining the presence of or measuring the quantity of the PTP 1D protein.

Also provided is a method for detecting in a nucleic acid containing sample the presence of a nucleic acid sequence encoding a normal or mutant PTP 1D protein, comprising:
(a) contacting the sample, or an extract thereof, with an oligonucleotide probe encoding at least a portion of the normal or mutant PTP 1D protein under hybridizing conditions; and
(b) measuring the hybridization of the probe to nucleic acid of the sample,
thereby detecting the presence of the nucleic acid sequence.

Preferably, the above method includes, before step (a), the step of selectively amplifying the amount of nucleic acid encoding the at least a portion of the normal or mutant PTP 1D protein.

The present invention is further directed to a method for identifying a compound capable of binding to PTP 1D protein, the method comprising:
(a) attaching the PTP 1D protein, or a compound-binding portion thereof, to a solid phase matrix;
(b) contacting a sample suspected of containing the compound with the matrix-bound PTP 1D protein, glycoprotein or portion thereof, allowing the compound to bind, and washing away any unbound material; and
(c) detecting the presence of the compound bound to the solid phase matrix.

In another embodiment is provided a method for isolating from a complex mixture a compound capable of binding to PTP 1D protein, the method comprising:
(a) attaching the PTP 1D protein, or a compound binding portion thereof, to a solid phase matrix;
(b) contacting the complex mixture with the matrix-bound PTP 1D protein, glycoprotein or portion thereof, allowing the compound to bind, and washing away any unbound material; and
(c) eluting the bound compound from the solid phase matrix, thereby isolating the compound.

In another embodiment, the present invention includes a method for determining whether a compound is capable of stimulating or inhibiting the phosphotyrosine phosphatase enzymatic activity of PTP 1D, the method comprising:
(a) contacting the compound with the PTP 1D protein in pure form, in a membrane preparation, or in a whole live or fixed cell, or with an enzymatically active fragment of the PTP 1D protein;
(b) incubating the mixture of step (a) for an interval sufficient for the compound to stimulate or inhibit the enzymatic activity;
(c) measuring the phosphotyrosine phosphatase enzymatic activity of the PTP 1D protein, glycoprotein or fragment;
(d) comparing the enzymatic activity to that of the PTP 1D protein, glycoprotein or fragment incubated without the compound, thereby determining whether the compound stimulates or inhibits the activity.

The present invention is also directed to a pharmaceutical composition for treating or preventing a disease associated with an abnormal PTP 1D protein, the composition comprising a PTP 1D protein, or a functional derivative thereof, and a pharmaceutically acceptable carrier.

In another embodiment, the invention provides a pharmaceutical composition for treating or preventing a disease associated with an abnormal PTP 1D protein having deficient enzymatic activity, the composition comprising a compound in an amount effective to stimulate phosphotyrosine phosphatase enzymatic activity of PTP 1D, and a pharmaceutically acceptable carrier.

Also provided is a pharmaceutical composition for treating or preventing a disease associated with an abnormal PTP 1D protein having supranormal enzymatic activity, the composition comprising a compound in an amount effective to inhibit phosphotyrosine phosphatase enzymatic activity of PTP 1D, and a pharmaceutically acceptable carrier.

The present invention includes a method for treating or preventing a disease associated with an abnormal PTP 1D protein in a subject, comprising administering to the subject a pharmaceutical composition as described above.

4. BRIEF DESCRIPTION OF THE DRAWINGS

FIG. 1 shows the sequence of a clone, called P158, which encodes a part of a novel PTP. Shown are both the DNA sequence [SEQ ID NO:6] and the deduced amino acid sequence [SEQ ID NO:7].

FIGS. 2A–2B shows the complete cDNA sequence [SEQ ID NO:4] and the deduced amino acid sequence [SEQ ID NO:5] of PTP 1D.

FIGS. 3A–3B shows the sequences of FIGS. 2A–2B, above with the SH2 and PTP domains boxed and the latter shaded. For convenience, approximately 4.7 kb between the termination codon TGA (1908–1911) and the polyadenylation signal are not shown.

Figure 7A:
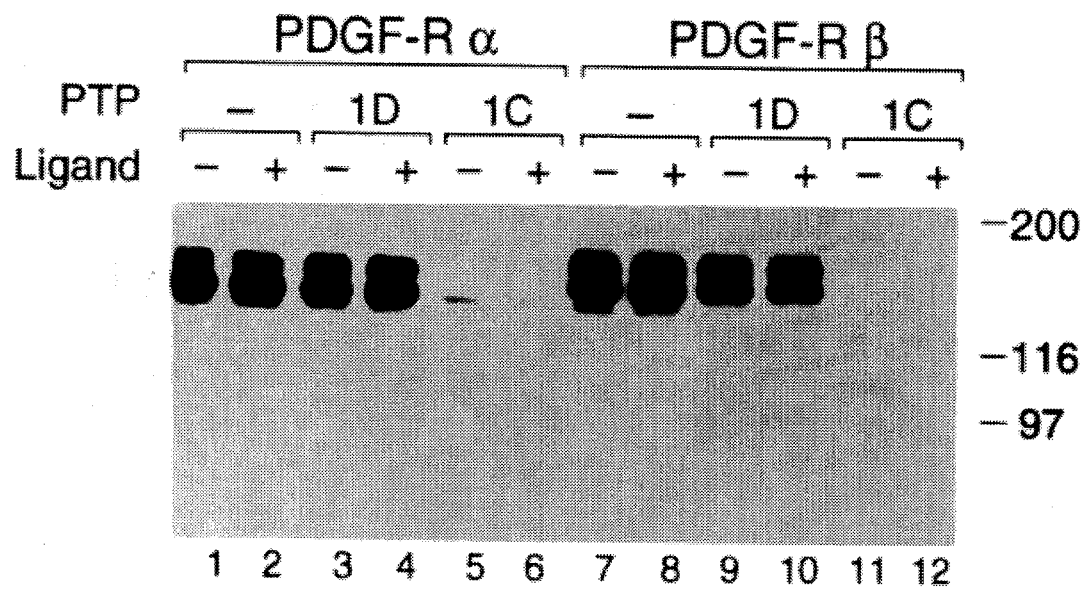
Figure 7B:
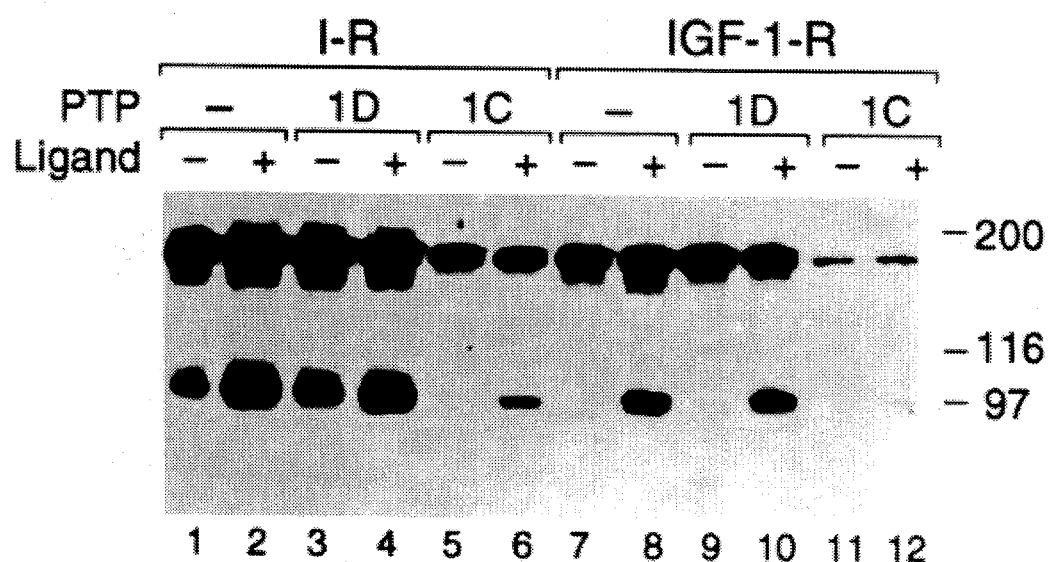
Figure 7C:
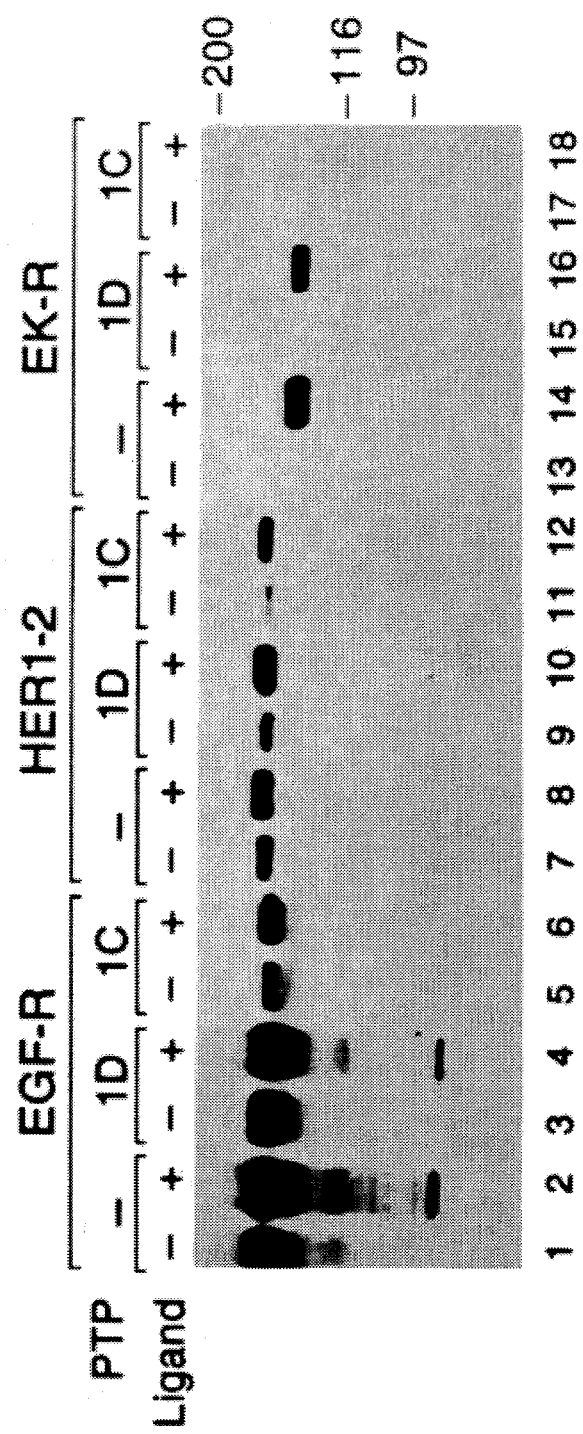

FIGS. 7A, 7C the effect of transient overexpression of PTP 1D and PTP 1C on RPTK tyrosine phosphorylation in human embryonic kidney fibroblasts of the 293 line. Cells were stimulated for 10 minutes with the indicated ligand, lysed, separated by SDS-PAGE, transferred to nitrocellulose and probed with the monoclonal anti-phosphotyrosine antibody 5E2. Molecular weight markers are indicated.

Figures 8A, 8B:
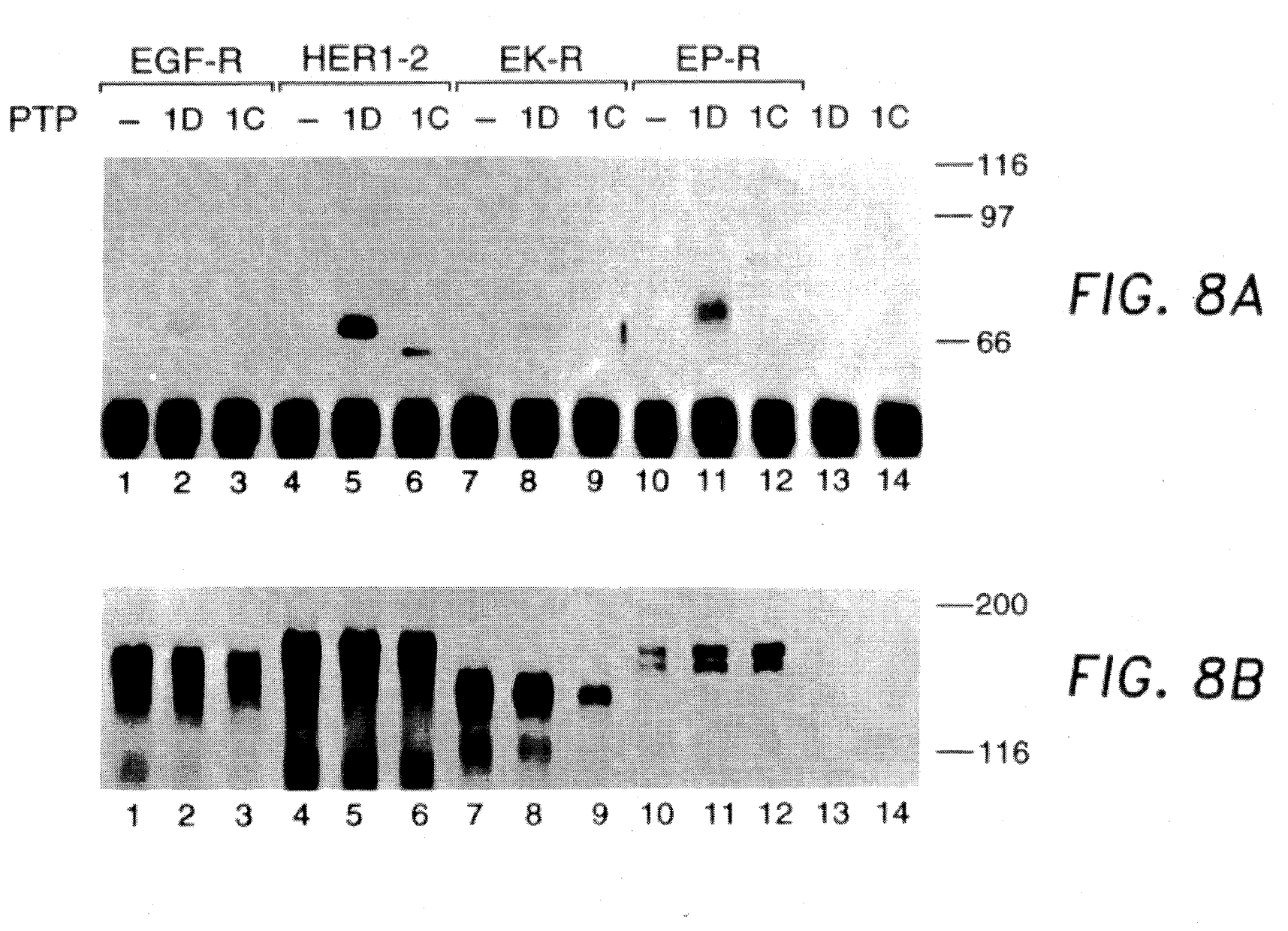

FIGS. 8A–8B shows the association PTP 1D and PTP 1C with EGF receptor-associated PTKs. After stimulation with 50 ng/ml EGF, the receptor material was immunoprecipitated with mAb 108.1. The precipitates were run in 7.5% SDS-PAGE, transferred to nitrocellulose, and probed with a mixture of rabbit antisera raised against PTP 1D and PTP 1C (upper panel). Samples in lanes 13 and 14 were transfected with PTPs alone. The lower panel shows the autoradiographic analysis of the precipitated RPTKs. Molecular weight markers are indicated.

Figure 9:
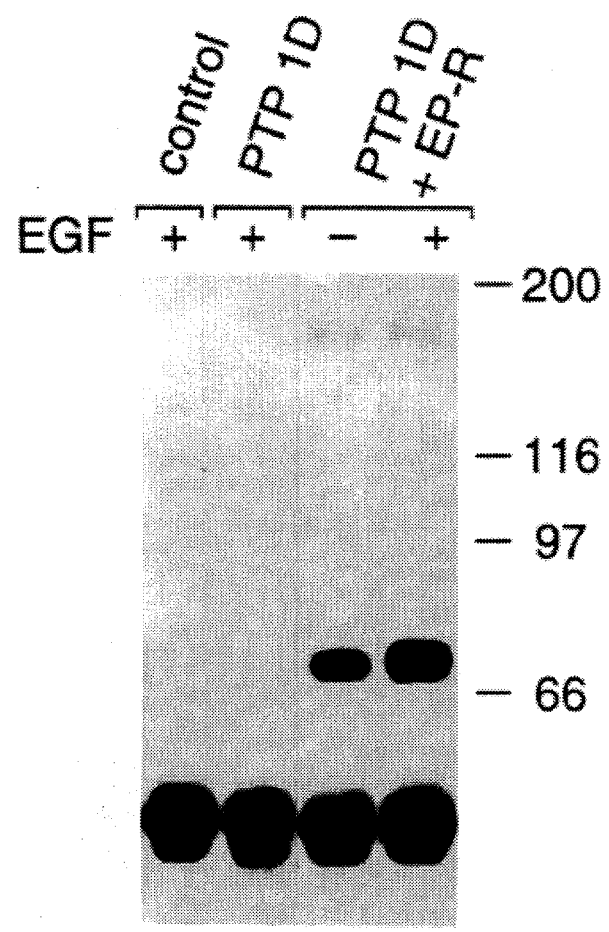

FIG. 9 shows phosphorylation of PTP 1D by activated EP-R. Immunoprecipitates of PTP 1D from 293 cell transfectants expressing either PTP 1D alone or with the EP-R chimera were subjected to immunoblot with antiphosphotyrosine antibodies. Expression vector transfected 293 cells were employed as negative controls.

Figure 10:
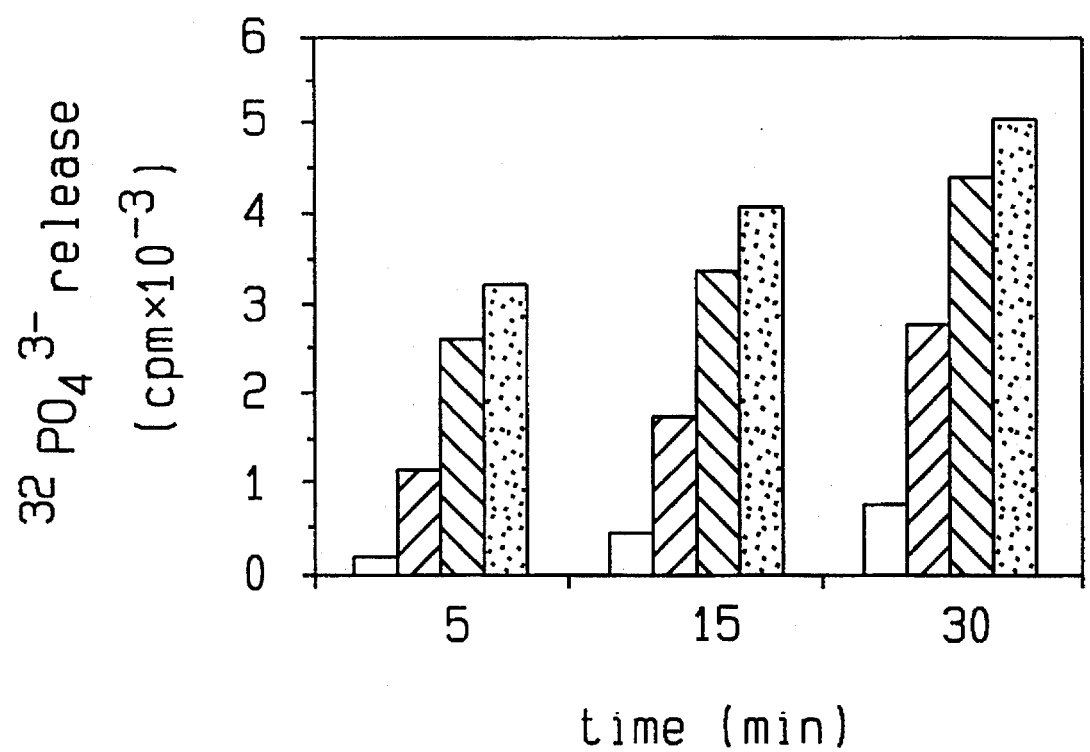

FIG. 10 shows the results of measuring PTP 1D phosphatase activity in vitro of the cell lysates shown in FIG. 9. The data of a representative experiment with two parallel measurements for each time point are shown. Immunoprecipitates from cells transfected with either control plasmid (open bar), PTP 1D expression vector (cross-hatched bar) or PTP 1D and EP-R expression plasmids together (stippled bar: −EGF; black bar: +EGF).

5. DETAILED DESCRIPTION OF THE INVENTION

The following table lists the single-letter abbreviations for amino acids that are in common use among protein chemists and are used herein.

| Amino Acid | Symbol | Amino Acid | Symbol |
|---|---|---|---|
| Glycine | G | Arginine | R |
| Alanine | A | Lysine | K |
| Valine | V | Histidine | H |
| Leucine | L | Phenylalanine | F |
| Isoleucine | I | Tyrosine | Y |
| Serine | S | Tryptophan | W |
| Threonine | T | Proline | P |
| Cysteine | C | Serine or Asparagine | S/N |
| Methionine | M | | |
| Aspartic Acid | D | Aspartic Acid or Asparagine | D/N |
| Asparagine | N | | |
| Glutamic Acid | E | Isoleucine or Valine | I/V |
| Glutamine | Q | | |
| | | Not Specified | X |

The present inventors previously identified a new subfamily ('PTP-D subfamily') of protein tyrosine phosphatases (PTPs). Members of the PTP-D family have significant structural differences from previously reported PTPs. The present inventors have now cloned and sequenced yet another PTP designated PTP-1D (FIGS. 2A–2B).

The term "subfamily" is used to indicate a group of PTPs which are structurally related at specific amino acid residues as specified above.

The expression "previously defined amino acid consensus sequences" refers to the conserved amino acid sequences in the catalytic phosphatase domains of known PTPs described in Krueger et al., supra, and Yi et al., supra.

Thus, in a preferred embodiment, the present invention relates to the PTP-1D protein FIGS. 2A–2B having the amino acid sequence SEQ ID NO:5, or a functional derivative thereof.

One embodiment of the present invention is a naturally occurring mammalian PTP-1D. Another embodiment comprises a recombinant mammalian PTP-1D. Yet another embodiment is a chemically synthesized mammalian PTP 1D protein. Methods for the synthesis of polypeptides of desired sequence on solid phase supports and their subsequent separation from the support are well-known in the art.

The preferred PTP-1D protein of the present invention is of human origin.

The naturally occurring PTP 1D protein is preferably substantially free of other proteins or glycoproteins with which it is natively associated. "Substantially free of other proteins or glycoproteins" indicates that the PTP 1D protein has been purified away from at least 90% (on a weight basis), and from even at least 99%, if desired, of other proteins and glycoproteins with which it is natively associated, and is therefore substantially free of them.

Such purification can be achieved by subjecting cells, tissue or fluid containing the PTP 1D protein to a standard protein purification technique, for example, immunoaffinity chromatography using an immunoadsorbent column to which is immobilized a monoclonal antibody (mAb) which binds to the protein.

Other useful types of affinity purification utilize a solid-phase substrate for the PTP which bind the catalytic phosphatase domain, or a ligand that binds to the extracellular receptor domain of a receptor-type PTP protein. Alternatively, or additionally, the PTP 1D protein is purified using a combination of standard methods, such as ammonium sulfate precipitation, molecular sieve chromatography, and ion exchange chromatography.

It will be understood that a mammalian PTP 1D protein of the present invention can be biochemically purified from a variety of cell or tissue sources. For preparation of a naturally occurring PTP 1D protein, tissues such as brain tissue, especially of human origin, are preferred. A preferred cellular source of nucleic acid encoding PTP-1D, or of the protein, is the cell line SK-BR-3, or the human breast cancer lines, BT-474 and T-47-D.

Because the gene for PTP 1D protein can be isolated or synthesized, PTP 1D protein can be synthesized substantially free of other proteins or glycoproteins of mammalian origin in a prokaryotic organism or in a non-mammalian eukaryotic organism, if desired. As intended by the present invention, a recombinant PTP 1D protein produced in mammalian cells, such as transfected COS, NIH-3T3, or CHO cells, for example, is either a naturally occurring protein sequence or is a modified protein sequence having amino acid deletions, insertions, substitutions or a combination thereof. Where a naturally occurring PTP 1D protein is produced by recombinant means, it is provided substantially free of the other proteins and glycoproteins with which it is natively associated.

Also provided herein are functional derivatives of a PTP 1D protein. By "functional derivative" is meant a "fragment," "variant," "analogue," or "chemical derivative" of the protein, which terms are defined below. A functional derivative retains at least a portion of the function of the PTP 1D protein, for example reactivity with an antibody specific for the PTP 1D protein, PTP enzymatic activity or ligand binding activity, which permits its utility in accordance with the present invention.

The term "fragment" is used to indicate a polypeptide which is derived from PTP 1D, preferably human PTP-1D, and has naturally occurring protein sequence. Such a fragment may be produced by proteolytic cleavage of the full-length protein. Preferably, the fragment is obtained recombinantly by appropriately modifying the DNA sequence encoding the PTP 1D protein to delete one or more amino acids at one or more sites of the C-terminal, N-terminal, and within the native sequence.

Fragments of a PTP 1D protein are useful for screening for compounds that are antagonists or agonists (as defined below). It is understood that such fragments may retain one or more characterizing portions of the native protein. Examples of such retained characteristics include: (a) PTP catalytic activity; (b) substrate specificity; (c) interaction with other molecules in the intact cell; (d) regulatory functions of PTP 1D; or (e) binding with an antibody specific for the native protein, or an epitope thereof.

Another functional derivative intended within the scope of the present invention is a PTP 1D variant with additional amino acids, the variant being derived from a naturally occurring PTP 1D protein by appropriately modifying the DNA coding sequence to add codons for one or more amino acids at one or more sites of the C-terminal, N-terminal, and within the native sequence. It is understood that such a variant having additional amino acids retains one or more characterizing portions of the native PTP 1D protein, as described above.

A preferred variant is one which has substituted amino acids, the variant being derived from a naturally occurring PTP 1D protein by appropriately modifying or mutating the DNA coding sequence to substitute one or more amino acids at one or more sites of the C-terminal, N-terminal, and within the native amino acid sequence. It is understood that such a variant having substituted amino acids retains one or more characterizing portions of the native PTP 1D protein as described above.

Any combination of deletion, insertion, and substitution may also be made to arrive at the final construct of a PTP 1D functional derivative, provided that the final construct possesses at least one desired activity or function of the intact PTP 1D protein, as described above.

The above examples are not intended to be in any way limiting to the scope of the invention claimed.

Obviously, the modifications or mutations that will be made in the DNA encoding the PTP 1D protein must not alter the reading frame and preferably will not create complementary regions that could produce secondary mRNA structure (see European Patent Publication No. EP 75,444).

At the genetic level, a functional derivative of PTP 1D protein with deleted, inserted or substituted amino acid residues ordinarily is prepared by site-directed mutagenesis (as exemplified by Adelman et al., *DNA* 2:183 (1983)) of nucleotides in the DNA coding the sequence, producing a modified coding sequence, thereafter expressing this recombinant DNA a prokaryotic or eukaryotic host cell (see below). The functional derivative of the PTP 1D protein typically exhibits the same qualitative biological activity as a native protein.

In another embodiment, a functional derivative of PTP 1D protein with amino acid deletions, insertions or substitutions (or a combination thereof) may be conveniently prepared by direct chemical synthesis, using methods well-known in the art.

Also included in the present invention is a "chimeric" PTP molecule, constructed from a another PTP in which one or more specific amino acid sequences are replaced with homologous sequence(s) from a PTP 1D. One example of such a chimeric molecule is a PTP 1D protein having a ligand-binding extracellular domain derived from another receptor-type PTP that is grafted onto a portion of the PTP 1D protein of the present invention. Other chimeric molecules include:

(a) Another PTP having the catalytic phosphatase domain of a PTP 1D protein of the present invention. In this case, the preferred number of amino acids is between 220 and 260;

(b) A PTP 1D protein in which part or parts of the catalytic domain has been replaced with homologous part(s) from other PTPs, such as members of the PTP-D subfamily.

As used herein, the term "homologous sequence or sequences" is defined as the sequence in two or more PTPs which are similarly positioned in the primary sequence and which may exhibit sequence homology. It should be emphasized that "homologous sequences" is not intended to be limited to two sequences with a high degree of homology.

Chimeric molecules are useful as tools for elucidating structure-function relationships and for identifying specific compounds such as drugs that interact with PTP 1D protein. A useful chimeric molecule is therefore one in which a certain portion of one molecule has been replaced with the similarly positioned, but divergent, sequence from another, otherwise homologous, molecule. The exchanged portions will quite often represent the parts of the molecules showing the greatest divergence. A preferred chimeric molecules include, but are not limited to, a PTP 1D protein with a ligand-binding extracellular domain that is an epidermal growth factor (EGF) receptor, a fibroblast growth factor (FGF) receptor, and the like. Genetically engineered chimeric receptors are well-known in the art. See, for example, Riedel et al., *Nature* 324:628–670 (1986).

A "chemical derivative" of the PTP 1D protein or peptide contains additional chemical moieties not normally a part of the protein. Covalent modifications of the protein or peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the PTP 1D protein or peptide to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., *PROTEINS: STRUCTURE AND MOLECULAR PROPERTIES,* W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences,* 16th ed., Mack Publishing Co., Easton, Pa. (1980).

In another aspect, the present invention relates to a nucleic acid construct which comprises a nucleotide sequence encoding the PTP 1D protein, or encoding a PTP 1D protein having amino acid deletions and/or and/or substitutions. Preferably the nucleic acid construct comprises a sequence shown in FIGS. 2A–2B.

The invention is further directed to the above nucleic acid in the form of an expression vector such as a recombinant expression vector, as well as prokaryotic and eukaryotic host cells containing the expression vector.

Also provided are methods for expressing a nucleic acid encoding PTP 1D protein. PTP 1D protein may be produced by culturing cells in a suitable nutrient medium under conditions which are conducive to the expression of such DNA encoding PTP 1D.

One of ordinary skill in the art will know how to identify and clone additional PTPs, of human or other mammalian species, which have sequence homology to the PTP 1D protein described herein, using the nucleic acid construct and oligonucleotides of the present invention without undue experimentation.

Furthermore, manipulation of the nucleic acid of the present invention allows the grafting of a particular ligand-binding extracellular domain from a particular receptor PTP onto a portion of PTP 1D protein, resulting in a chimeric protein as described above.

Nucleic acid constructs encoding PTP 1D protein, encoding a functional derivative thereof, such as a variant with amino acid deletions, insertions or substitutions, or encoding a chimeric PTP 1D protein as described above, can be used in gene therapy. An abnormal or dysfunctional PTP 1D protein which results in a disease or disorder, may be replaced by infusing or grafting cells of the desired lineage (such as hemopoietic cells, for example) which have been transfected and are capable of expressing a normal PTP 1D protein. Alternatively, or additionally, cells capable of expressing a chimeric PTP 1D protein with a receptor portion which binds to a ligand of choice (e.g., EGF) can be used for such gene therapy.

The nucleic acid constructs that are recombinant DNA molecules of the present invention can be produced through any of a variety of means, such as, for example, DNA or RNA synthesis, or more preferably, by recombinant DNA techniques. Techniques for synthesizing such molecules are disclosed by, for example, Wu et al. (*Prog. Nucl. Acid. Res. Molec. Biol.* 21:101–141 (1978)). Procedures for constructing recombinant molecules in accordance with the above-described method are disclosed by Sambrook et al., *MOLECULAR CLONING: A LABORATORY MANUAL,*

Second Edition, Cold Spring Harbor Press, Cold Spring Harbor, N.Y. (1989).

The 3' terminus of a recombinant DNA molecule of this invention is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support may be of any form, (for example, a sheet, rod, sphere, ovoid, etc. Procedures for such immobilization are well known to these of ordinary skill. In the most preferred embodiment, the 3' end of the recombinant DNA molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, preferably a large number, of such recombinant DNA molecules to the support.

Oligonucleotides representing a portion of the sequence encoding the PTP 1D protein are useful for screening for the presence in a cell or tissue of a gene which encodes PTP 1D and for cloning such a gene. Techniques for synthesizing such oligonucleotides are disclosed by, for example, Wu et al. (supra).

Because the genetic code is degenerate, more than one codon may be used to encode a particular amino acid (Watson, J. D. et al., *MOLECULAR BIOLOGY OF THE GENE*, 4th Ed., Benjamin/Cummings Publishing Co., Menlo Park, Calif. (1987)). Therefore, one or more different oligonucleotides can be identified which is capable of encoding one or several amino acids. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Use of such "codon usage rules" (Lathe et al., *J. Molec. Biol.* 183:1–12 (1985)), allows the identification of a single oligonucleotide, or a set of oligonucleotides, that contains a theoretical most probable nucleotide sequence capable of encoding the PTP 1D sequence. Although occasionally an amino acid sequence may be encoded by only a single oligonucleotide, usually the sequence may be encoded by any of a set of similar oligonucleotides. Whereas all members of this set may encode the peptide fragment, only one member of the set contains the nucleotide sequence that is identical to that of the gene. Because this member is capable of hybridizing to DNA even in the presence of the other members of the set, it is possible to employ the unfractionated set of oligonucleotides in the same manner in which one would employ a single oligonucleotide to clone the gene that encodes the protein of interest.

The oligonucleotide, or set of oligonucleotides, containing the theoretical "most probable" sequence capable of encoding the PTP 1D fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate a PTP 1D gene (Sambrook et al., supra).

A suitable oligonucleotide, or set of oligonucleotides, which is capable of encoding a fragment of the PTP 1D gene (or which is complementary to such an oligonucleotide, or set of oligonucleotides) is identified (using the above-described procedure), synthesized, and hybridized by means well known in the art, to a DNA, preferably cDNA, preparation derived from cells which are capable of expressing a PTP 1D gene. Single stranded oligonucleotide molecules complementary to the "most probable" PTP 1D coding sequences can be synthesized using procedures which are well known to those of ordinary skill in the art (Belagaje et al., *J. Biol. Chem.* 254:5765–5780 (1979); Maniatis et al., In: MOLECULAR MECHANISMS IN THE CONTROL OF GENE EXPRESSION, Nierlich et al., eds., Academic Press, NY, 1976; Wu et al., supra; Khorana, R. G., *Science* 203:614–625 (1979)). DNA synthesis may be done using an automated synthesizers. Techniques of nucleic acid hybridization are disclosed by Sambrook et al. (supra), and by Haymes et al. (In: NUCLEIC ACID HYBRIDIZATION, A PRACTICAL APPROACH, IRL Press, Washington, D.C., 1985), which references are herein incorporated by reference.

Techniques such as, or similar to, those described above have successfully enabled the cloning of genes for human aldehyde dehydrogenases (Hsu et al., *Proc. Natl. Acad. Sci. USA* 82:3771–3775 (1985)), fibronectin (Suzuki et al., *EMBO J.* 4:2519–2524 (1985)), the human estrogen receptor gene (Walter et al., *Proc. Natl. Acad. Sci. USA* 82:7889–7893 (1985)), tissue-type plasminogen activator (Pennica et al., *Nature* 301:214–221 (1983)) and human term placental alkaline phosphatase complementary DNA (Kam et al., *Proc. Natl. Acad. Sci. USA* 82:8715–8719 (1985)).

In an alternative way of cloning the PTP 1D gene, a library of expression vectors is prepared by cloning DNA, preferably cDNA, from a cell capable of expressing PTP 1D into an expression vector. The library is then screened for members capable of expressing a protein which binds to a ligand specific for the PTP 1D protein, preferably an antibody, and which contain a nucleotide sequence that encodes a polypeptide of the same amino acid sequence as PTP 1D (or fragments thereof). In this embodiment, DNA, preferably cDNA, is extracted and purified from a cell which is capable of expressing PTP 1D protein. The purified cDNA is fragmented (by shearing, endonuclease digestion, etc.) to produce a pool of DNA or cDNA fragments. Fragments from this pool are then cloned into an expression vector in order to produce a genomic library of expression vectors whose members each contain a unique cloned DNA or DNA fragment.

An "expression vector" is a vector which (due to the presence of appropriate transcriptional and/or translational control sequences) is capable of expressing a DNA (or cDNA) molecule which has been cloned into the vector, thereby producing the protein. Expression of the cloned sequences occurs when the expression vector is introduced into an appropriate host cell. For a prokaryotic expression vector, the appropriate host cell is any prokaryotic cell capable of expressing the cloned sequences. Analogously, for a eukaryotic expression vector, the appropriate host cell is any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing PTP 1D in order to produce a prokaryotic genomic expression vector library. Procedures for preparing cDNA and for producing a genomic library are disclosed by Sambrook et al. (supra).

A DNA sequence which encodes the PTP 1D protein of this invention, a functional derivative thereof or a chimeric molecule thereof, may be recombined with vector DNA in accordance with conventional techniques, including use of blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations, disclosed in Sambrook et al. (supra), are well-known in the art.

A nucleic acid construct, such as DNA, is said to be "capable of expressing" a polypeptide if it contains nucleotide sequences containing transcriptional and translational regulatory information and such sequences are "operably linked" to nucleotide coding sequences. "Operably linked" refers to a linkage in which the regulatory DNA sequences and the DNA sequence to be expressed are connected in such a way as to permit transcription (and ultimately, translation). The precise nature of the regulatory regions needed for gene expression may vary from organism to organism. Generally, a "promoter region" is required which, in prokaryotes, contains both the promoter (which directs the initiation of RNA transcription) and DNA sequences which, when transcribed, signal the initiation of protein synthesis. A promoter is a double-stranded DNA or RNA sequence which is capable of binding RNA polymerase and promoting the transcription of an "operably linked" nucleic acid sequence. Such regulatory regions will normally include those 5'-non-coding sequences involved with initiation of transcription and translation, such as the TATA box, capping sequence, CAAT sequence, and the like.

If desired, the non-coding region 3' to the coding sequence, obtained by the above-described methods, may be retained for its transcriptional termination regulatory sequences, such as termination and polyadenylation. Where the transcriptional termination signals are not satisfactorily functional in the expression host cell, then a 3' region functional in that host cell may be substituted.

Two DNA sequences (such as a promoter region sequence and a PTP 1D protein coding sequence) are said to be operably linked if the nature of the linkage between the two DNA sequences does not (1) result in the introduction of a frame-shift mutation, (2) interfere with the ability of the promoter region to direct the transcription of the coding sequence, or (3) interfere with the ability of the coding sequence to be transcribed. A promoter region is operably linked to a DNA sequence if the promoter is capable of effecting transcription of that DNA sequence.

Certain RNA polymerases exhibit a high specificity for promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e., transcribe) only one strand of the two strands of a duplex DNA template. This strand selection, determined by the orientation of the promoter sequence, determines the direction of transcription.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" nucleic acid sequence are operably linked if transcription commencing in the promoter sequence will produce an RNA transcript of the operably linked second sequence. In order to be "operably linked" it is not necessary that two sequences be immediately adjacent to one another.

The promoter sequences of the present invention may be either prokaryotic, eukaryotic or viral. Suitable promoters are repressible, or, more preferably, constitutive. Examples of suitable prokaryotic promoters include promoters capable or recognizing the T4 (Malik et al., *J. Biol. Chem.* 263:1174–1181 (1984); Rosenberg et al., *Gene* 59:191–200 (1987); Shinedling et al., *J. Molec. Biol.* 195:471–480 (1987); Hu et al., *Gene* 42:21–30 (1986)), T3, Sp6, and T7 (Chamberlin et al., *Nature* 228:227–231 (1970); Bailey et al., *Proc. Natl. Acad. Sci.* (U.S.A.) 8024:2814–2818 (1983); Davanlook et al., *Proc. Natl. Acad. Sci.* (U.S.A.) 81:2035–2039 (1984)) polymerases; the $P_R$ and $P_L$ promoters of bacteriophage lambda (*The Bacteriophage Lambda*, Hershey, A.D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen et al., *J. Bacteriol.* 162:176–182 (1985)) and the σ28-specific promoters of *B. subtilis* (Gilman et al., *Gene* 32:11–20 (1984)); the promoters of the bacteriophages of Bacillus (Gryczan, T. J., In: *THE MOLECULAR BIOLOGY OF THE BACILLI*, Academic Press, Inc., NY (1982)); Streptomyces promoters (Ward et al., *Mol. Gen. Genet.* 203:468–478 (1986)); the int promoter of bacteriophage lambda; the bla promoter of the β-lactamase gene of pBR322, and the CAT promoter of the chloramphenicol acetyl transferase gene of pBR325, etc. Prokaryotic promoters are reviewed by Glick, B. R. (*J. Indust. Microbiol.* 1:277–282 (2987)); Cenatiempo, Y. (*Biochimie* 68:505–516 (1986)); Watson et al, supra; Gottesman, S. (*Ann. Rev. Genet.* 18:415–442) (1984)).

Preferred eukaryotic promoters include the promoter of the mouse metallothionein I gene (Hamer et al., *J. Mol. Appl. Gen.* 1:273–288 (1982)); the SV40 early promoter (Benoist et al., *Nature* 290:304–310 (1981)); and the yeast gal4 gene promoter (Johnston et al., *Proc. Natl. Acad. Sci* (USA) 79:6971–6975 (1982); Silver et al., *Proc. Natl. Acad. Sci.* (USA) 81:5951–5955 (1984)). All of the above listed references are incorporated by reference herein.

Strong promoters are preferred. Examples of such preferred promoters are those which recognize the T3, SP6 and T7 polymerases, the $P_L$ Promoter of the mouse metallothionein I gene. A most preferred promoter for eukaryotic expression of PTP 1D is SV40 promoter such as that driving transcription in the pLSV vector (Livneh et al., (1986) *J. Biol. Chem.* 261, 12490–12497). The sequences of such polymerase recognition sites are disclosed by Watson et al., supra.

In a further aspect, the present invention relates to an antibody which is capable of specifically recognizing PTP 1D protein or of specifically recognizing an epitope of PTP 1D protein.

The recombinantly expressed or naturally occurring PTP 1D protein, and/or a specific antibody for the protein may be used in a method of diagnosing a disease or condition with abnormal expression or activation of PTP 1D. The present invention provides a method for evaluating the presence and the level of normal or mutant PTP 1D protein in a subject. Absence, or more typically, low expression of the PTP 1D protein, or presence of a mutant PTP 1D protein, in an individual may serve as an important predictor of susceptibility to oncogenic transformation and the development of cancer. Alternatively, over-expression of PTP 1D protein, possibly due to a mutant receptor/enzyme system insensitive to negative regulation, or due to overabundance of a stimulatory ligand in the body, may serve as an important predictor of susceptibility to diabetes.

The antibody of the present invention may be used to detect the presence of, or measure the quantity or concentration of, PTP 1D protein, in a cell, a cell or tissue extract, or a biological fluid.

The term "antibody" is meant to include polyclonal antibodies, monoclonal antibodies (mAbs), humanized or chimeric antibodies, single chain antibodies, anti-idiotypic (anti-Id) antibodies, and epitope-binding fragments of any of the above.

Polyclonal antibodies are heterogeneous populations of antibody molecules derived from the sera of animals immunized with an antigen, such as PTP 1D protein, or an antigenic functional derivative thereof.

A mAb, which is a substantially homogeneous population of antibodies to a particular antigen, may be obtained by methods known to those skilled in the art. See, for example, Kohler et al., *Nature* 256:495–497 (1975) and U.S. Pat. No. 4,376,110. Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo production makes this the presently preferred method of production. Briefly, cells from an individual hybridoma are injected intraperitoneally into pristane-primed mice to produce ascites fluid containing high concentrations of the desired mAb. The mAb, of preferably of the IgM or IgG isotype, may be purified from such ascites fluids, or from culture supernatants, using column chromatography methods or affinity chromatography methods well known to those of skill in the art.

A chimeric antibody is a molecule in which different portions are derived from different animal species, such as those having variable region derived from a murine mAb and a human immunoglobulin constant region. Chimeric antibodies and methods for their production are well-known in the art (Cabilly et al., *Proc. Natl. Acad. Sci. USA* 71:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268270 (1985); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Sahagan et al., *J. Immunol.* 137:1066–1074 (1986); Robinson et al., International Patent Publication #PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 140:1041–1043 (1988)). These documents are hereby incorporated by reference.

For human therapeutic purposes, a mAb or a chimeric antibody can be "humanized" by producing a human constant region chimera, where even parts of the variable regions, in particular the conserved or framework regions of the antigen-binding domain, are of human origin, and only the hypervariable regions are non-human. See for example, UK Patent Publication GB 2188638A); Harris et al., PCT Publication WO9204381 (Mar. 19, 1992); Riechmann et al., *Nature* 332:323–327 (1988).

In yet another embodiment, the antibody is a single chain antibody formed by linking the heavy and light chain fragment of the Fv region via an amino acid bridge, resulting in a single chain polypeptide (Bird, *Science* 242:423–426 (1988); Huston et al., *Proc. Natl. Acad. Sci. USA* 85:5879–5883 (1988); and Ward et al., *Nature* 334:544–546 (1989)).

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, a mAb generated against PTP 1D protein of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a PTP 1D epitope. The anti-Id mAbs thus have their own idiotypic epitopes, or "idiotopes" structurally similar to the epitope being evaluated, such as PTP 1D protein.

As used herein, the term "antibody" is also meant to include both intact molecules as well as fragments thereof, such as, for example, Fab and $F(ab')_2$, which are capable of binding antigen. Fab and $F(ab')_2$ fragments lack the Fc fragment of intact antibody, clear more rapidly from the circulation, and may have less non-specific tissue binding than an intact antibody (Wahl et al., *J. Nucl. Med* 24:316–325 (1983)). It will be appreciated that Fab and $F(ab')_2$ and other fragments of the antibodies useful in the present invention may be used for the detection and quantitation of PTP 1D protein according to the methods disclosed herein for intact antibody molecules. Such fragments are typically produced by proteolytic cleavage, using enzymes such as papain (to produce Fab fragments) or pepsin (to produce $F(ab')_2$ fragments).

The antibodies, or fragments of antibodies, useful in the present invention may be used to quantitatively or qualitatively detect the presence of cells which express PTP 1D protein. This can be accomplished by immunofluorescence techniques employing a fluorescently labeled antibody (see below) coupled with light microscopic, flow cytometric, or fluorimetric detection.

The antibodies (or fragments thereof) useful in the present invention may be employed histologically, as in immunofluorescence or immunoelectron microscopy, for in situ detection of PTP 1D protein. In situ detection may be accomplished by removing a histological specimen from a patient, and applying thereto a labeled antibody of the present invention. The antibody (or fragment) is preferably applied by overlaying the labeled antibody (or fragment)

onto a biological sample. Through the use of such a procedure, it is possible to determine not only the presence of PTP 1D protein but also its distribution in the examined tissue. Using the present invention, those of ordinary skill will readily perceive that any of a wide variety of histological methods (such as staining procedures) can be modified in order to achieve such in situ detection. Such assays for PTP 1D protein typically comprise incubating a biological sample, such as a biological fluid, a tissue extract, freshly harvested cells such as lymphocytes or leukocytes, or cells which have been incubated in tissue culture, in the presence of a detectably labeled antibody capable of identifying PTP 1D protein, and detecting the bound antibody by any of a number of techniques well-known in the art.

The biological sample may be brought in contact with a solid phase support or carrier such as nitrocellulose, or other solid support which is capable of immobilizing cells, cell particles or soluble proteins. The support may then be washed with suitable buffers followed by treatment with the detectably labeled PTP 1D-specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-PTP 1D antibody may be determined according to well known methods. Those skilled in the art will be able to determine operative and optimal assay conditions for each determination by employing routine experimentation.

One of the ways in which the PTP 1D-specific antibody can be detectably labeled is by linking the same to an enzyme and use in an enzyme immunoassay (EIA) (Voller, A., "The Enzyme Linked Immunosorbent Assay (ELISA)", *Diagnostic Horizons* 2:1–7, 1978)) (Microbiological Associates Quarterly Publication, Walkersville, Md.); Voller, A. et al., *J. Clin. Pathol.* 31:507–520 (1978); Butler, J. E., *Meth. Enzymol.* 73:482–523 (1981); Maggio, E. (ed.), *ENZYME IMMUNOASSAY,* CRC Press, Boca Raton, Fla., 1980; Ishikawa, E. et al., (eds.) *ENZYME IMMUNOASSAY,* Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colon-metric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect PTP 1D protein through the use of a radioimmunoassay (RIA) (see, for example, Weintraub, B., *Principles of Radioimmunoassays,* Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The present invention also relates to a method for detecting the presence of a nucleic acid construct encoding PTP 1D protein, or a nucleic acid construct encoding a mutant PTP 1D protein, in a subject, comprising:

(a) contacting a cell or an extract thereof from said subject with an oligonucleotide probe encoding at least a portion of said normal or mutant PTP 1D protein under hybridizing conditions; and (b) measuring the hybridization of said probe to the nucleic acid of said cell, thereby detecting the presence of said nucleic acid construct.

The method may comprise an additional step (c) before step (a), which provides selectively amplifying the amount of nucleic acid encoding the PTP 1D protein. Preferably, the amplification is accomplished using the polymerase chain reaction (PCR; see below).

Oligonucleotide probes encoding various portions of the PTP 1D protein (see above) are used to test cells from a subject for the presence of DNA or RNA sequence encoding a PTP 1D protein. Techniques for synthesizing such probes are disclosed by for example, Wu et al., supra. A preferred probe would be one directed to the nucleic acid sequence encoding at least four amino acid residues, and preferably at least five amino acid residues, of a PTP 1D protein of the present invention (see Examples, below). Qualitative or quantitative assays can be performed using such probes. For example, Northern analysis is used to measure expression of a PTP 1D mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224); and Sambrook et al., (supra), which documents are herein incorporated by reference.)

An in vitro enzymatic method termed the "polymerase chain reaction" (PCR) is capable of increasing the concentration of such desired nucleic acid molecules. (Mullis et al., *Cold Spring Harbor Symp. Quant. Biol.* 51:263–273 (1986); Erlich, H., EP 50424, EP 84796, EP 258017, EP 237362; Mullis, K., EP 201184; Mullis et al., U.S. Pat. No. 4,683, 202; Erlich, H., U.S. Pat. No. 4,582,788; and Saiki et al., U.S. Pat. No. 4,683,194).

The present invention also relates to a method for identifying in a chemical or biological preparation a compound capable of binding to a PTP 1D protein, comprising:

(a) attaching the PTP 1D protein or a compound-binding portion thereof to a solid phase matrix;

(b) contacting the chemical or biological preparation with the solid phase matrix produced in step (a), allowing the compound to bind, and washing away any unbound material;

(c) detecting the presence of the compound bound to the solid phase, thereby identifying the compound. The above method may further include the step of:

(d) eluting the bound compound, thereby isolating the compound.

By the term "compound capable of binding to PTP 1D protein" is meant a naturally occurring or synthetically produced molecule which interacts with PTP 1D outside of the catalytic site of the phosphatase domain. (By the "catalytic site" is meant the smallest, contiguous part of PTP 1D which contains phosphatase enzymatic activity.) Such a compound may directly or indirectly modulate the enzymatic activity of the PTP 1D protein. Examples of such compounds are (i) a natural substrates, primarily an intracellular protein which interacts with and may be dephosphorylated by PTP 1D protein; (ii) naturally occurring molecules produced by other cell types.

By a "compound-binding portion" of PTP 1D protein is meant a part of the molecule which is outside of the catalytic site. Any part of the PTP 1D protein which is not part of the catalytic site may be a compound-binding portion. A "compound-binding portion" may be prepared from a naturally occurring or recombinantly expressed PTP 1D protein by proteolytic cleavage followed by conventional purification procedures known to those of skill in the art. Alternatively, the compound-binding portion may be produced by recombinant technology known to those of skill in the art by expressing only these parts of PTP 1D in suitable cells.

In a still further aspect, the present invention relates to a method of screening for a PTP "antagonist," defined as a molecule which directly or indirectly inhibits the enzymatic activity or activation of PTP-1D. In a further aspect, the present invention relates to a method of screening for a PTP "agonist," defined as a molecule which directly or indirectly increases the enzymatic activity or activation of PTP 1D protein.

PTP 1D protein of the present invention is useful in methods for screening drugs and other agents which are capable of activating or inhibiting the phosphatase activity, and thereby affecting major pathways of cellular metabolism. By attaching an intact PTP 1D protein or a fragment thereof, to a solid phase matrix, an affinity probe is created which can be used to screen biological products or chemical agents for their capacity to interact with PTP 1D on the basis of their binding activity. Bound material can then be eluted from the affinity probe in purified form.

A PTP 1D protein, or a functional derivative thereof, for example, having amino acid deletions and/or insertions and/or substitutions while maintaining phosphatase enzymatic activity, can be used for testing of compounds capable of enhancing or inhibiting the phosphatase activity. The ability of a compound under test to modify phosphatase activity can be tested in an in vitro system wherein the test compound is added to a purified PTP 1D protein, or a functional derivative thereof having enzymatic activity, and the effects on enzyme activity is measured using standard enzymological procedures well-known to those of ordinary skill in the art.

A suitable fragment of a PTP 1D protein for use in screening may be prepared by limited proteolytic treatment of the naturally occurring or recombinantly expressed PTP 1D protein. Alternatively, suitable fragment(s) of PTP 1D may be produced by recombinant technology. As an example, which is not intended to be in any way limiting to the scope of the invention claimed, it may be preferable to use only the catalytic domains for screening purposes. Such catalytic domains, which consist only of the minimum number of amino acids needed for enzymatic activity, could be produced either alone or as part of a fusion protein in suitable hosts (e.g., *E. coli*) by recombinant technology well known to those of ordinary skill in the art.

Alternatively, the action of a compound on PTP activity can be measured in a whole cell preparation using live or fixed cells, or a membrane fraction derived from live or fixed cells. This method is useful for screening compounds acting directly on the enzymatic portion of PTP 1D protein. A test compound is incubated with cells, for example, transfected COS or NIH-3T3 cells, or with a membrane preparation derived therefrom, which express high amounts of PTP 1D protein. The amount of cellular phosphotyrosine is then measured, using methods well-known in the art (Nonegger, et al., *Cell* 51:199–209 (1987); Margolis et al., supra). The results are compared to results obtained in the absence of the test compound, or in the absence or presence of a known activator of PTP 1D protein. In such tests, the action of the test compound in the presence of an activator of tyrosine kinase can also be measured. A compound which stimulates PTP activity will result in a net decrease in the amount of phosphotyrosine, whereas a compound which inhibits PTP activity will result in a net increase in the amount of phosphotyrosine.

In the case of growth factor receptors RPTKs, such as the epidermal growth factor receptor (EGF-R) and for platelet-derived growth factor receptor (PDGF-R), tyrosine phosphorylation is linked to cell growth and to oncogenic transformation. Activation of a PTP, leading to dephosphorylation, would serve as a counterregulatory mechanism to prevent or inhibit growth, and might serve as an endogenous regulatory mechanism against cancer. Thus, mutation or dysregulation of this receptor-enzyme system may promote susceptibility to cancer.

The insulin receptor is also a tyrosine kinase, and phosphorylation of tyrosine in cells bearing insulin receptors would be associated with normal physiological function. In contrast to the case of cell growth and cancer, activation of a PTP would counteract insulin effects. Subnormal PTP levels or enzymatic activity would act to remove a normal counterregulatory mechanism. Perhaps more important, though, over-activity, or inappropriate activation, of a PTP would be expected to inhibit or totally prevent the action of insulin on cells, leading to diabetes (of an insulin-resistant variety). Thus, susceptibility to diabetes may be associated with PTP dysregulation.

Therefore, the methods of the present invention for identifying normal or mutant PTP 1D genes, or for measuring the amount or activity of PTP 1D protein, associated with a cell or tissue, can serve as methods for identifying susceptibility to cancer, diabetes, or other diseases associated with alterations in cellular phosphotyrosine metabolism.

The invention also relates to the use of an antagonist or an agonist of PTP 1D, as identified using the methods described herein, in a pharmaceutical composition intended for treatment of a disease or condition with abnormal expression of PTP 1D. Alternatively, the pharmaceutical composition described herein may be used to treat a disease associated with normal PTP 1D activity but a molecular defect downstream from PT 1D in the signal transduction pathway. The pharmaceutical composition may typically be in a form for systemic or topical injection or infusion and may, as such, be formulated with a suitable carrier for injection or infusion.

The present invention also relates to a method for preventing or treating a disease or condition associated with activation of PTP 1D, the method comprising administering to a patient in need thereof, an effective dose of:
(a) PTP 1D protein, or a functional derivative thereof, as described above;
(b) an antibody specific for a PTP 1D epitope; or
(c) a molecule or compound that stimulates or inhibits the PTP enzymatic activity of PTP 1D.

Interactions of PTP 1D with particular PTKs are described in detail, below in Section 11. Based on these interactions, the present invention also includes methods for identifying the specific site of PTP 1D interaction with a PTK. Using the methods described herein, and biochemical and molecular biological methods well-known in the art, it is possible to identify the portions or the proteins involved in this interactions. For example, site-directed mutagenesis of DNA encoding either the PTP 1D or the kinase may be used to destroy or inhibit the interaction between the two molecules.

Thus, an antagonist of this interaction may comprise a peptide or a functional derivative thereof, which will prevent the interaction between PTP 1D and the kinase molecule. An agonist will promote the interaction.

Based on the foregoing, the present invention further provides an assay for identifying a compound, such as a small molecule, which can block the interaction of PTP 1D and a kinase. For example, a cell transfected to coexpress PTP 1D and a tyrosine kinase of choice, in which the two proteins interact, can be incubated with an agent suspected of being able to inhibit this interaction, and the effect on the PTP 1D-kinase interaction measured. Any of a number of means for measuring the interaction and its disruption are available, for example, the methods described in Section 11, below. Similarly, the present invention provides an assay method to identify and test an agonist compound which stabilizes and promotes the PTP 1D-kinase interaction, for example, activating the phosphatase enzymatic activity, using the same approach described above for a potential antagonist.

Having now generally described the invention, the same will be more readily understood through reference to the following examples which are provided by way of illustration, and are not intended to be limiting of the present invention, unless specified.

6. EXAMPLE: IDENTIFICATION OF NOVEL PTP DESIGNATED PTP 1D USING PCR

Confluent cultures of the human breast cancer cells of the line SK-BR-3 (ATCC HTB 30) were lysed by treatment with guanidinium-thiocyanate according to Chirgwin J. M. et al., *Biochemistry* 18:5294–5299 (1979)). Total RNA was isolated by CsCl— gradient centrifugation. Poly $(A)^+$ RNA was isolated on an oligo(dT) column (Aviv et al., *Proc. Natl. Acad. Sci. USA* 69:1408–1412 (1972)). First-strand cDNA was synthesized from 5 μg poly $(A)^+$ RNA using avian myeloblastosis virus (AMV) reverse transcriptase (Boehringer-Mannheim). One-tenth of the cDNA was subjected to the PCR using standard conditions (Erlich, H. E., 1989, supra). The following pool of primers was used for the amplification:
A. Sense primer, corresponding to the amino acid sequence D/E/G S/N D/N Y I N A (SEQ ID NO:8), corresponding to residues 63–69 in PTP 1B (Charbonneau et al., 1989, supra).

| EcoRi | |
|---|---|
| 1) GGAATTCGA(GATC)TC(GATC)GA(TC)TA(TC)AT(ACT)AA(TC)GC | [SEQ ID NO:9] |
| 2) GGAATTCGA(GATC)A(GA)(TC)GA(TC)TA(TC)AT(ATC)AA(TC)GC | [SEQ ID NO:10] |
| 3) GGAATTCGG(GATC)TC(GATC)(GA)A(TC)TA(TC)AT(ATC)AA(TC)GC | [SEQ ID NO:11] |

B. Antisense primer, corresponding to the amino acid sequence K C A/D Q/E Y W P [SEQ ID NO:12], corresponding to residues 120–126 in PTP-1B (Charbonneau et al., supra)

| BamHI | |
|---|---|
| 4) CGGGATCCGGCCA(AG)TA(TC)T(GC)(GATC)GC(AG)CA(TC)TT | [SEQ ID NO:13] |
| 5) CGGGATCCGGCCA(AG)TA(TC)T(GC)(GA)TC(AG)CA(TC)TT | [SEQ ID NO:14] |

It is expected that an important site of interaction is a phosphorylated tyrosine residue in either or both of the proteins. Once this site has been identified, the present invention provides means for promoting or inhibiting this interaction, depending upon the desired biological outcome.

Thirty-five PCR cycles were carried out using 10 μg of the pooled primers (annealing at 37° C. for 2 min; extension at 72° C. for 1.30 min; denaturation at 94° C. for 1 min). The reaction product was subjected to polyacrylamide gel electrophoresis (PAGE).

The fragments of the expected size (~220 bp) were isolated, digested with the restriction enzymes EcoRI and BamHI, and subcloned into the pBluescript vector (Stratagene) using standard techniques (Ausubel, F. M. et al., eds., *Current Protocols in Molecular Biology*, John Wiley & Sons, New York, 1988). The subcloned PCR products were sequenced by the dideoxy chain termination method (Sanger et al., *Proc. Natl. Acad. Sci. USA* 74:5463–5467 (1977)) using Sequenase (United States Biochemical, Cleveland, Ohio, USA).

One clone, called P158 was identified to be a novel sequence. The nucleotide and deduced amino acid sequence of this clone are shown in FIG. 1.

| | |
|---|---|
| PTP 1B [SEQ ID NO:17]: | N A S L I K M E E A Q      R S Y I L T Q G |
| TC PTP [SEQ ID NO:18]: | N A S L V D I E E A Q      R S Y I L T Q G |
| PTP 1C [SEQ ID NO:19]: | N A N Y I K N Q L L G P D E N A      K T Y I A S Q G |
| PTP 1D [SEQ ID NO:5]: | N A N I I M P E F E T K C N N S K P K K S Y I A T Q G |

7. EXAMPLE: cDNA CLONING OF PTP 1D

The partial cDNA sequence of the new PTP, designated PTP 1D, which was identified by PCR, was used to screen a lambda ZAP cDNA library from SK-BR-3 cells. Five μg Poly(A)$^+$ RNA was used for the construction of this unidirectional library using the ZAP cDNA kit (Stratagene, Cat. No. 200400).

In brief, first-strand synthesis was done with the primer 5'-CTCGAG(T)$_{17}$-3' [SEQ ID NO:15] Moloney Murine Leukemia virus reverse transcriptase. Second-strand synthesis was performed in the same tube using RNAse H, DNA polymerase 1, and T4 DNA polymerase. EcoRI linkers were added after methylation, and the cDNA preparation was size selected (>1000 bp) on a 1% agarose gel and inserted into EcoRI/XhoI predigested lambda ZAP II arms. The resulting library had a complexity of 1.8×10$^6$ recombinant phages.

About 1.2×10$^6$ independent phage clones were plated and transferred to nitrocellulose filters following standard procedures (Sambrook et al., supra). The filters were hybridized to the EcoRI/BamHI DNA fragment of clone P158, which had been radiolabeled using 50 μCi [α$^{32}$P]ATP and the Random Primed DNA Labeling Kit (Boehringer Mannheim, Cat No. 1004760). The subcloning of positive bacteriophage clones into pBluescript vector was simplified by the in vivo excision protocol as recommended by the manufacturer (Stratagene). The coding portion of the longest cDNA insert (~6.2 kilobases) was sequenced by the chain termination method (described in Section 5, above).

The sequence has an open reading frame of 1560 bp at its 5' end. The sequence from nucleotide position 710 to 915 is identical to the above-described PCR clone. Additional conserved sequence motifs are found in the PTP domain, e.g., HCSAGIGR [SEQ ID NO:5] at positions 458–464 in the new sequence, corresponding to positions 214–220 in the PTP 1B sequence). The sequence did not comprise an ATG with an upstream stop codon. Therefore the SK-BR-3 cDNA library was rescreened at low stringency using an $^{32}$P-labeled oligonucleotide probe (oligo #218, 5'-TTT CTT GTG CGT GAG AGC CTC AGC CAG CCT GGA GAC TTC GTG CTT TCT GTC C-3' [SEQ ID NO:16]) corresponding to nucleotides 658–709 of PTP 1C (Shen S.-H. et al., supra).

One clone containing an insert of 1200 bp was found to overlap the initially identified sequence and contained an ATG at nucleotide position 131 with an upstream stop codon at position 85.

The complete cDNA sequence and the predicted amino acid sequence of the new clone are shown in FIGS. 2A–2B. Because of the relationship to PTP 1C and to the cytosolic PTP 1B, the novel gene was given the name PTP 1D. The predicted molecular weight of the protein chain is about 70 kDa.

The PTP 1D amino acid sequence contained surprising sequence motifs. Upon comparison of PTP 1D with other known intracellular PTPs, the present inventors were able to identify an insertion region within the otherwise highly conserved PTP domain. Whereas the PTP 1C sequence is only 5 amino acids longer than PTP 1B and TC PTP, PTP 1D contained an insertion of 8 amino acids (corresponding to amino acids no. 317 to 324 in SEQ ID NO:5):

Inclusion of the PTP 1D, csw (corkscrew) and PTP 1C in the sequence comparisons revealed that the conserved sequence QGP is altered in the SH2 domain-containing phosphatases to QGC.

PTPs with an insertion of 3 or more amino acids at the indicated position are defined to be members of a new PTP subfamily.

8. EXAMPLE: EXPRESSION OF PTP 1D IN HUMAN CELLS AND TISSUES BY NORTHERN ANALYSIS

8.1. PTP 1D Expression in Normal Tissue

Figure 4:
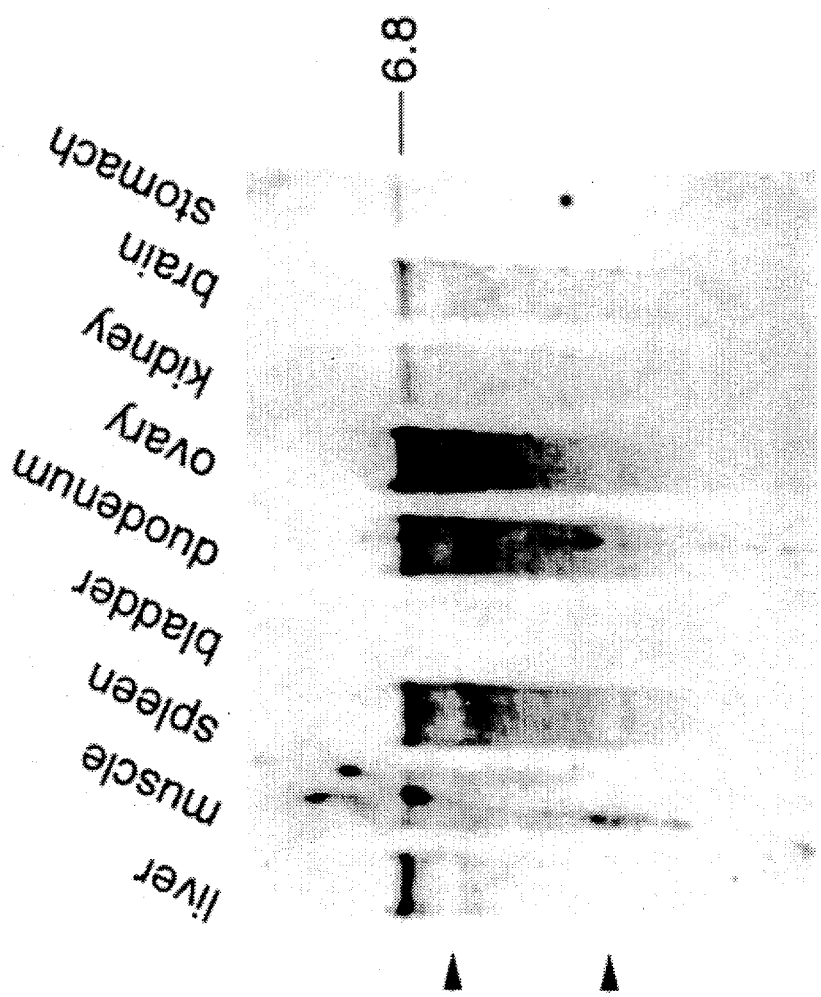
FIG. 4 is a blot showing the expression of PTP 1D in several human tissues.

Total RNA was isolated from each of the following human tissues: liver, skeletal muscle, spleen, bladder, duodenum, ovary, kidney, brain, and stomach. Poly(A)$^+$ RNA was isolated as described above, separated on an agarose gel containing 2.2M formaldehyde and blotted on a nitrocellulose filter (Schleicher & Schuell). Five μg of poly (A)$^+$ was loaded per lane. The filter was hybridized with a $^{32}$P-labeled EcoRI/BglII DNA fragment corresponding to nucleotides 1–705 of the PTP1D sequence. The labeling was done with the Random Primed DNA Labeling Kit (Cat. no. 1004760, Boehringer Mannheim, Germany) according to the manufacturer's instructions. Subsequently, the filter was applied to X-ray film at −70° C. with an intensifying screen. FIG. 4 shows the expression of PTP 1D in human tissues.

Surprisingly, PTP 1D was found to be expressed in many different tissues. The highest expression was in brain, whereas expression was lower in skeletal muscle, ovary, and stomach. Liver, duodenum, and kidney contain only a very low level of transcripts. No signal could be detected using RNA from bladder and spleen.

This expression pattern is in sharp contrast to the pattern for the related PTP, PTP 1C. Expression of PTP 1C is highly restricted, predominantly to hematopoietic tissues and cells (Yi et al., supra).

8.2. PTP 1D Expression in Human Breast Cancer Cell Lines

Figure 5:
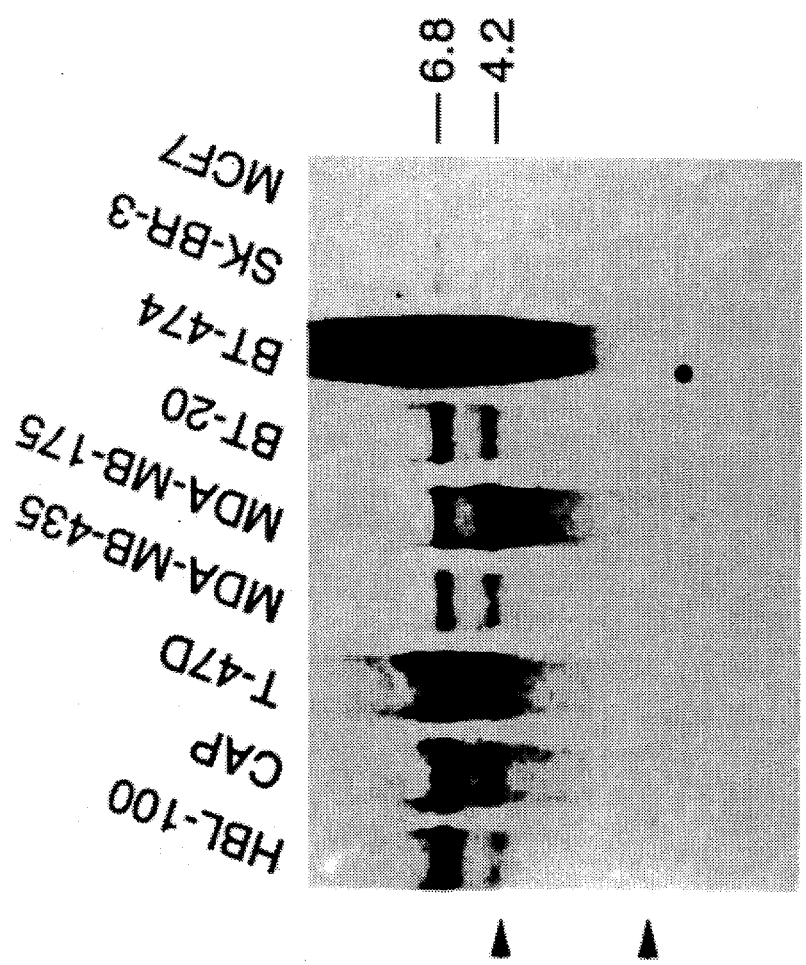
FIG. 5 is a blot showing the expression of PTP 1D and HER2 in human breast cancer cell lines.

Northern blot analysis was also performed on RNA from several human breast cancer cell lines using the methods described above. The Northern blot was subsequently reprobed with a cDNA fragment of the human oncogene HER2 (Human Epidermal Growth Factor Receptor Type 2). HER2 overexpression has been shown to correlate directly with cell transformation and mammary cancer (Slamon, D. J. et al., *Science* 235:177–182 (1987)). The expression of PTP 1D and HER2 in human breast cancer cell lines is shown in FIG. 5.

The novel PTP 1D of the present invention has the remarkable property of being overexpressed in a coordinate fashion with HER2 in the majority of cell lines analyzed. Thus, both are expressed at low levels in MCF-7 cells, whereas both genes are overexpressed in BT-474 and in T-47-D cells.

9. EXAMPLE: DETECTION OR MEASURING PTP-1D PROTEIN IN A CELL

9.1. Production of Antibodies with Specificity for PTP 1D

The cDNA insert of one of the identified phage clones was digested with appropriate restriction enzymes to release a 550-bp fragment (corresponding to nucleotides 226 to 780 in the PTP 1D sequence of FIGS. 2A–2B). The DNA fragment was cloned in-frame into the pGEX-3X Glutathione S-transferase (GST) gene fusion vector (Pharmacia, Cat. no. 27-4803-01).

The bacterial expression of the GST fusion protein was induced after overnight culture by adding 0.5 mM isopropyl β-D-thiogalactoside (IPTG) for 3 hours. The fusion protein was purified from the supernatant of ultrasonicated bacterial lysates by batch chromatography on Glutathione Sepharose 4B (Pharmacia), (Smith et al., supra).

Figure 6:
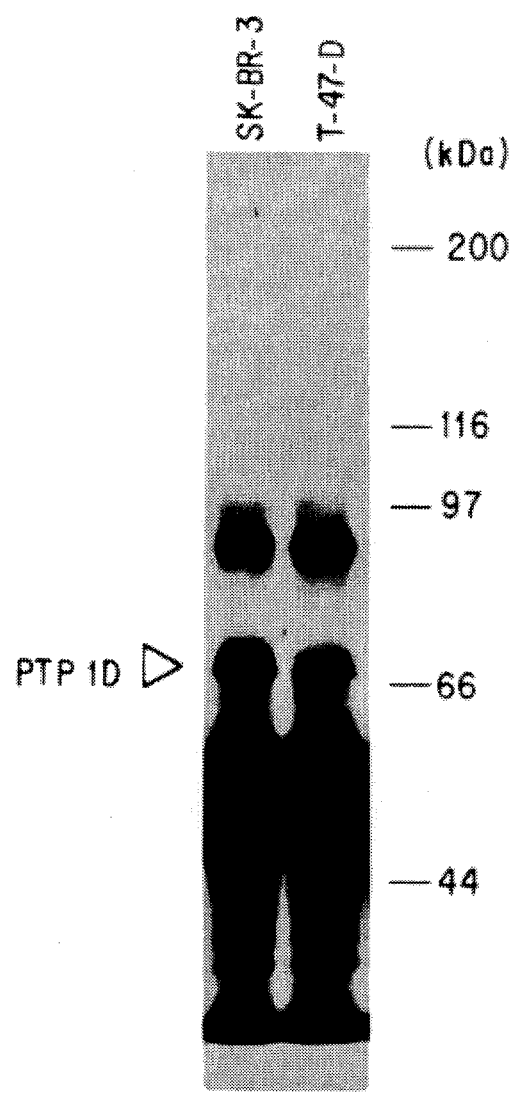
FIG. 6 is a Western blot of lysates of the human breast cancer cell lines SK-BR-3 and T-47-D which endogenously express PTP 1D (7.5% polyacrylamide gel transferred onto nitrocellulose filter). The blot was probed with a rabbit antiserum made by immunizing with the GST-PTP 1D fusion protein.

A rabbit was immunized by injection of the GST-PTP 1D fusion protein (500 µg) in an equal volume of complete Freund's adjuvant. The rabbit was boosted twice with the same antigen. After the second boost, the rabbit serum was tested for antibody reactivity in immunoprecipitation (Western blot) with lysates of the human breast cancer cell lines SK-BR-3 and T-47-D which endogenously express PTP 1D. The samples were loaded on a 7.5% polyacrylamide gel and after electrophoresis transferred onto a nitrocellulose filter (Schleicher & Schuell). The blot was probed with the same antibody as above and developed using the ECL Western blotting detection system following the manufacturer's instructions (Amersham International, UK; Cat. no. RPN 2108). The results are shown in FIG. 6.

The antiserum was found to immunoprecipitate proteins from the two cell preparations, including a peak at about 70 kDa corresponding to PTP 1D.

10. EXAMPLE: IDENTIFICATION OF A MOLECULE THAT STIMULATES OR INHIBITS ENZYMATIC ACTIVITY OF PTP 1D

The cDNA containing the entire coding region of PTP 1D, or an enzymatically active portion thereof, is inserted into the mammalian expression vector pcDNA I (Cat. No. V490-20, Invitrogen, San Diego, Calif.) using standard techniques (Ausubel et al., supra). The 293 cell transient expression system described by Gorman et al., *Virology* 171:377–385 (1989) is used for production of enzymatically active PTP. Using standard techniques, the 293 cells are cultured in 5% $CO_2$ at 37° C. in Dulbecco's Modified Eagle Medium supplemented with 10% (v/v) fetal calf serum (DMEM-FCS) (Gibco, Life Technologies Ltd., Paisley, Scotland).

Thus, 10 µg of the plasmid construct containing the PTP 1D cDNA are mixed with 0.5 ml 0.25M $CaCl_2$ and 0.5 ml 2×BBS (50 mM N,N-bis(2-hydroxyethyl)-2aminoethanesulfonic acid (BES), 280 mM NaCl, 1.5 mM $Na_2HPO_4$) and used for transfection of $1.5\times10^6$ 203 cells in a 10 cm Petri dish as described by Chen et al., *Mol. Cell. Biol.* 7:2745–2752 (1987). The cells are incubated 24 hours at 37° C. under 3% $CO_2$ after the addition of the Ca phosphate-DNA precipitate, then washed once in DMEM-FCS and incubated in fresh medium for additional 24 hours at 37° C. under 5% $CO_2$. The medium is removed and the cells lysed in 1.0 ml of lysis buffer (20 mM HEPES pH 7.5, 150 mM NaCl, 10% glycerol, 1.0% Triton X-100, 1.5 mM $MgCl_2$, 4 mM EGTA (Sigma ED2SS), 10 µg/ml aprotinin, 1 mM PMSF). The cell lysates are centrifuged at 2500×g for 2 minutes at 4° C. The supernatant is removed and 100 µl aliquots are quick-frozen in liquid nitrogen and stored at −70° C. until use.

The PTP 1D preparation may also be a lysate of the SK-BR-3 cell line (ATCC HTB 30). PTP 1D may also be obtained from other cell lines or from normal tissues which express this protein, as described above.

Three different substrates are used for the evaluation of potential inhibitors or stimulators of the PTP enzymatic activity: (1) p-nitrophenyl phosphate (pNP-P; Sigma 104-0); (2) $^{32}$P-labeled Raytide (Oncogene Science Inc., Manhasset, N.Y.); or (3) $^{32}$P-labeled bovine myelin basic protein (MBP). Substances which are found to decrease or increase the activity of the PTP of the present invention against one or more of these substrates are analyzed further.

The enzymatic activity of PTP 1D on pNP-P is measured essentially as described by Tonks, N.K. et al., *J. Biol. Chem.* 263:6731–6737 (1988). Using microtiter plates, 10 µl of the 293 lysate from above are incubated with 100 µl of pNP-P (30 and 100 mM, respectively) at room temperature. The absorbance is read at 1 minute intervals in Dynatech MR5000 reader. The substance being analyzed for stimulatory or inhibitory activities is added to the PTP 1D/293 cell lysate 5 minutes prior to the addition of pNP-P.

The activity of PTP 1D towards $^{32}$P-labeled Raytide™ is measured essentially as described by Krueger et al., supra). The synthetic peptide Raytide is labeled with $^{32}$P using the tyrosine kinase p60$^{c\text{-}src}$ according to the manufacturer's instructions (Oncogene Science) with minor modifications. In brief, 2 µl of p60$^{c\text{-}src}$ are mixed with 20 µl Raytide (1 mg/ml) and 108 µl of kinase buffer (50 mM HEPES pH 7.5 containing 10 MM $MgCl_2$, 0.2% (v/v) β-mercaptoethanol, 30 µM ATP and 50 µCi [$\gamma^{32}$P]ATP). The mixture is incubated at 37° C. for 16 hours, and the reaction is stopped by addition of 500 µl of 20% (w/v) trichloroacetic acid (TCA) in 20 mM $NaH_2PO_4$ and 100 µl of 5 mg/ml of acetylated bovine serum albumin. The mixture is centrifuged, the precipitate is washed three times in 20% TCA/20 mM $NaH_2PO_4$, and finally redissolved in 0.2M Tris-Cl pH 8.0.

Myelin basic protein (Sigma Chemical Co.) is labeled using a procedure similar to that described above for Raytide (Guan et al., *Nature* 350:359–362 (1991)). Thirty µg of MBP is labeled in a 60 µl reaction containing the following components: 50 mM HEPES buffer pH 7.5, 10 mM $MgCl_2$, 0.067% β-mercapto-ethanol, 0.05 mM ATP including 150 µCi[$\gamma^{32}$P]ATP and 4 units p43$^{v\text{-}abl}$ kinase (Oncogene Science). The mixture is incubated for 60 minutes at 30° C., and the reaction is stopped by addition of ice-cold TCA to a final concentration of 20%. After 30 minutes on ice, the precipitate is washed three times in 20% TCA and redissolved in 100 µl $H_2O$.

For enzyme assay with Raytide or MBP, 5 µl of concentrated (10×) PTP buffer (25 mM HEPES pH 7.3, 5 mM EDTA, 10 mM dithiothreitol) are mixed with: (a) 5 µl $^{32}$P-labeled Raytide or MBP (corresponding to 10–20×10$^4$ cpm); (b) 5, 10 and 25 μl, respectively, of the PTP-D1/293 cell lysate, and (c) H$_2$O to a final volume of 50 μl. The reaction is stopped after incubation for 30 minutes at 37° C. In the case of Raytide, the reaction is stopped by addition of 0.75 ml acidic charcoal mixture (Krueger et al., supra) as follows: 0.9M HCl, 90 mM sodium pyrophosphate, 2 mM NaH$_2$PO$_4$, 4% (v/v) Norit A (Sigma)). After mixing and centrifugation, 400 μl of the supernatant are removed and the radioactivity measured. When using MBP as a substrate, the reaction is stopped by addition of 20% TCA (final volume). The amount of $^{32}$P the supernatant is then measured.

The substances to be analyzed for stimulatory or inhibitory activities are added to the PTP-D1/293 cell lysate 5 minutes prior to initiation of the assays.

Molecules or agents that stimulate or inhibit the PTP activity of PTP 1D are identified by the above means.

11. EXAMPLE: INTERACTIONS OF PTP 1D WITH PROTEIN TYROSINE KINASES

To investigate PTP 1D-specific function in intact cells, the substrate specificity of PTP 1D and its association with a panel of RPTKs was examined and compared to that of PTP 1C. A system developed in the present inventors' laboratory was employed which allows transient co-overexpression of multiple transfected genes.

11.1. Co-Expression of RTKases with PTP 1D

PTP 1D cDNA expression constructs in a cytomegalovirus promoter-based vector were transfected into human 293 embryonic kidney cells together with expression plasmids for seven RPTKs. In the case of HER2/neu and p145$^{c-kit}$, chimeric receptors, HER 1-2 and EK-R were used, wherein the respective kinase functions were under the control of an EGF-R extracellular domain (Lee, J. et al., *EMBO J.* 8:167 (1989); Herbst, R. et al., *J. Biol Chem.* 266:19908 (1991)) (FIG. 7).

Semiconfluent 293 cells (human embryonic kidney fibroblast; ATCC CRL 1573) were either transfected with RPTK expression plasmids alone or together with human PTP 1D or mouse PTP 1C expression vectors (Gorman, C. M. et al., *Virology* 171:377 (1989); Lammers R. et al., *J. Biol. Chem.* 265:16886 (1990)). After 24 hours of serum starvation, cells were stimulated for 10 minutes with the appropriate ligand (see FIG. 7) and lysed. Aliquots of cell lysate were separated by SDS-PAGE, transferred to nitrocellulose and probed with the monoclonal anti-phosphotyrosine antibody 5E2. Blots were developed using the ECL detection system (Amersham). Molecular weight markers are indicated.

In these experiments, the apparent absence of a ligand effect on PDGF-R and EGF-R phosphorylation was due to very high overexpression and constitutive activation of a basal activity for these receptors in this system. Surprisingly, a remarkable difference was detected in dephosphorylation activity of PTP 1D as compared to PTP 1C, despite approximately equivalent, high expression levels.

Coexpression of PTP 1C led to partial or complete dephosphorylation of overexpressed PDGF-Rα and β subunits and the β subunits and unprocessed precursors of insulin receptor (I-R) and insulin-like growth factor-1 receptor (IGF-1-R), but had marginal effects on EGF-R and HER1-2 phosphorylation states.

In contrast, PTP 1D had no significant effect on any of the RPTKs examined, with the exception of a weak dephosphorylation activity on the EK-R chimera (FIG. 7C, lanes 14–16).

11.2. Specific Interactions of PTP with RTKase

A different picture emerged when the possible association of PTPs with coexpressed RPTKs was examined. The results suggested that PTP 1C and PTP 1D specifically interacted with distinct kinase domains.

To standardize the experimental parameters, three chimeric RPTKs having EGF-R extracellular domains were tested (HER1-2, EK-R, EP-R) (Seedorf, K. et al., *J. Biol Chem.* 266:12424 (1991)), as was EGF-R itself (FIGS. 8A–8B).

After serum starvation, metabolic labelling with [$^{35}$S]-L-methionine overnight, and stimulation with 50 ng/ml EGF for 10 minutes, the EGF-R and the chimeric receptors were immunoprecipitated with the monoclonal antibody 108.1, specific for the EGF-R extracellular domain. This strategy eliminated the influence of possible differences in growth factor or antibody properties on the experiment, and permitted quantitative comparison of the results. The precipitates were extensively washed, boiled in SDS sample buffer, and analyzed by 7.5% SDS-PAGE. After transfer to nitrocellulose, the blot was probed with a mixture of rabbit antisera raised against PTP 1D and PTP 1C. These antisera had been obtained by immunizing rabbits with fusion proteins consisting of glutathione S-transferase (Pharmacia) and portions of N-terminal sequences of PTP 1D (residues 28–219) or PTP 1C (residues 55–302), respectively.

As shown in FIG. 8A (upper panel), PTP 1C was associated only with the HER1-2 chimera (lane 6). In contrast, PTP 1D associated strongly with HER2/neu (HER1-2) and PDGF-Rβ (EP-R) cytoplasmic domains, and associated with lower affinity with EGF-R and c-kit (EK-R). Notably, the 68 kDa PTP 1D band in lanes 2, 5 and 8, resulting from EGF-R, HER1-2, and EK-R, respectively, shifted to a higher apparent M$_r$ in lane 11, suggesting phosphorylation as a result of interaction with activated EP-R.

11.3. Tyrosine Phosphorylation of PTP 1D and Stimulation of Phosphatase Activity To examine whether PTP 1D could serve as a substrate for the PDGF-Rβ kinase, 293 cells were transfected with PTP 1D and EP-R as described above, and cell lysates were analyzed by anti-PTP 1D antibody immunoprecipitation, PAGE, and immunoblotting with antiphosphotyrosine antibody. Expression vector-transfected 293 cells were employed as negative controls.

FIG. 9 demonstrates clear ligand-induced tyrosine phosphorylation of a PTP 1D band, which now migrated at 69 kDa; weak coprecipitation of a larger tyrosine-phosphorylated protein of about 180 kD was also detected, probably the EP-R chimera (Seedorf, K. et al., *J. Biol Chem.* 266:12424 (1991)).

Certain specific cellular signal transduction pathways involve sequential protein-protein interactions which lead to structural modifications, changes in substrate conformation, and, in some cases, enzymatic activity. Thus, an experiment was conducted to test whether tyrosine phosphorylation by the PDGF-Rβ kinase influenced the catalytic activity of PTP 1D.

Identical aliquots of anti-PTP 1D immunoprecipitates from 293 cells coexpressing EP-R and PTP 1D were tested for phosphatase enzymatic activity by measuring their ability to release phosphate from $^{32}$P-poly(Glu-Tyr), after substrate precipitation in TCA (Tung, H. Y. L. et al., *Anal. Biochem.* 161:412 (1987)). Immune complexes bound to Protein A-Sepharose (Pharmacia) were incubated with $^{32}$P-labelled substrate (10,000 cpm) for the indicated time (see FIG. 10) at 37° C. After precipitation with 1.5 volumes of 20% TCA, the release of $^{32}P$ in the supernatant was determined by Cerenkov counting. The data of a representative experiment with two parallel measurements for each time point are shown in FIG. 10. The basal activity of immunoprecipitated PTP 1D was enhanced in samples containing coexpressed EP-R; this activity increased significantly upon ligand stimulation of intact transfected cells. The higher PTP 1D activity, seen even in the absence of ligand, reflected its phosphorylation state under these conditions (FIG. 9) and is a consequence of EP-R activation due to overexpression. For the first time, these results clearly demonstrated the regulation of PTP catalytic activity by direct interaction with, and tyrosine phosphorylation by, a ligand-activated RPTK.

11.4. Discussion

To approach the problems of PTP target specificity and activity regulation, the present investigators studied the functional properties of the novel PTP of the present invention, designated PTP 1D, which was derived from SK-BR3 mammary carcinoma cells. Coexpression of PTP 1D and a homologous PTP, PTP 1C, with a panel of seven RPTKs of different structural subclasses revealed surprisingly different properties of the two structurally similar SH2-domain bearing PTPs.

While PTP 1C displayed promiscuous activity on autophosphorylated EGF-R, HER2/neu, I-R, IGF1-Rα and β, PDGF-R, and SCF-R/c-kit cytoplasmic domains, leading to partial or complete dephosphorylation, PTP 1D had no activity in the same experiment. This was particularly unexpected, since both PTPs were coexpressed in several mammary carcinoma cell lines. Indeed, these findings strongly suggested distinct regulatory functions for these PTP 1C and PTP 1D.

These results raised several possibilities: PTP 1D may not have functioned at all in signal down-regulation of RPTK; alternatively, the specific RPTK target for PTP 1D may not have been among the kinases examined. Furthermore, the apparent lack of specificity demonstrated by PTP 1C may (a) result from abnormal overexpression, which could have caused overactivation and apparent loss of specificity, or (b) reflect the requirement for additional factors needed for the definition of specificity but which were absent from 293 embryonic fibroblasts.

A remarkable difference existed between PTP 1D and PTP 1C in their ability to form complexes with RPTK cytoplasmic domains. Thus, while PTP 1C was only coprecipitated with a chimeric EGF-receptor containing the HER2/neu cytoplasmic domain, PTP 1D exhibited a broader spectrum of interactions with affinity for all receptors tested FIGS. 8A–8B. This result was in contrast with the apparent inactivity of PTP 1D in dephosphorylating RPTKs in intact transfected cells FIGS. 7A–7C.

The present inventors interpreted these results as follows: PTP 1D interacts tightly, presumably via its SH2 sequences, with phosphotyrosine residues in the activated PDGF-Rβ cytoplasmic domain, thereby protecting them from dephosphorylation. This protects the receptor from inactivation. In turn, PTP 1D is tyrosine-phosphorylated, which activates its catalytic function and may lead to activation of a positive signal modulation. This interpretation draws support from genetic studies of Drosophila csw PTP, which is homologous to PTP 1D, and which acts downstream from the RPTK-encoding gene, torso, and apparently cooperates with a raf homolog and the transcription factors, tailess and huckebein, in the determination of terminal structures of the Drosophila embryo (Perkins, L. A. et al., *Cell* 70:225 (1992)).

Previous reports have shown that the LAR and CD45 PTPs can serve as substrates for Ser/Thr and tyrosine kinases in vitro and in intact cells (Pot D.A. et al., *J. Biol. Chem.* 266:19688 (1991); Stover, D. R. et al., *Proc. Natl. Acad. Sci. USA* 88:7704 (1991)). Moreover, Ser/Thr phosphorylation of CD45 has been implicated in the regulation of its catalytic activity, since both the extent of CD45 phosphorylation and its activity are decreased in T lymphocytes treated with $Ca^{++}$ ionophores (Ostergaard, H. L. et al., *Science* 253:1423 (1991)).

In contrast, the results presented above show that an increase in tyrosine phosphorylation of PTP 1D by the PDGF-Rβ kinase, in intact cells, correlated with proportional enhancement of its catalytic activity. Thus, the present findings (1) represent the first example of significant PTP interaction with specific PTK targets, and (2) provide evidence for tyrosine phosphorylation-mediated regulation of PTP activity by the PDGF-R kinase.

In analogy to csw/torso genes in Drosophila, this interaction of PTP and PTK appears to result in a positive effect on the PDGF signal transduction pathway. Such a concept finds support in the involvement of CD45 in lck tyrosine kinase signalling within the T cell receptor complex (Mustelin, T. et al., *Oncogene* 5:809–813 (1990)), and in the finding by the present inventors' laboratory that PTKs of the src family can be activated by PTP 1α and PTP 1D-induced dephosphorylation (see, also, Zheng, X. M. et al., *Nature* 359:336 (1992)). These observations point to the importance of the interactions between PDGF-R, src-type PTKs, and PTP 1D, and open new avenues to the exploration of the precise mechanisms which underlie PDGF-R specific signal transduction. The present findings not only shed now light on the molecular events leading to the generation of signals by RPTKs, but also provide clues to the role of PTPs in diseases involving cell proliferation, including cancer.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated and purified nucleic acid molecule substantially free of nucleotide sequences with which the molecule is natively associated comprising a nucleotide sequence that (a) encodes the protein tyrosine phosphatase 1D amino acid sequence (SEQ ID No:5); or (b) which hydbridizes to the complement of the nucleotide sequence of (a).

2. An isolated and purified nucleic acid molecule substantially free of nucleotide sequences with which the molecule is natively associated comprising a nucleotide sequence that (a) hybridizes under stringent conditions to a nucleic acid molecule that encodes the amino acid sequence SEQ ID No: 5, and encodes a naturally occurring PTP 1D protein; or (b) which hybridizes to the complement of the nucleotide sequence of (a).

3. A nucleic acid molecule which comprises (a) a nucleotide sequence that encodes a polypeptide having the amino acid sequence shown in SEQ ID No: 5 which contains amino acid residues 6–101, 112–215, 216–275, 276–517, or 518–593; or (b) which hybridizes to the the complement of the nucleotide sequence of (a).

4. A nucleic acid molecule which comprises (a) a nucleotide sequence that encodes a PTP 1D protein or glycoprotein lacking at least one through four domains which contain amino acid residues 6–101, 112–215, 216–275, 276–517, or 518–593 shown in SEQ ID No: 5; or (b) which hybridizes to the the complement of the nucleotide sequence of (a).

5. A cloning vector containing the nucleic acid molecule of claim 1, 2, 3 or 4.

6. An expression vector containing the nucleic acid molecule of claim 1, 2, 3 or 4 operatively linked with a nucleotide sequence containing transcriptional and translational regulatory information that controls expression of the nucleotide sequence in a host cell.

7. A transformed or transfected host cell containing the nucleic acid molecule of claim 1, 2, 3 or 4.

8. A transformed or transfected host cell containing the nucleic acid molecule of claim 1, 2, 3 or 4 operatively linked with a nucleotide sequence containing transcriptional and translational regulatory information that controls expression of the nucleotide sequence in a host cell.

9. The transformed or transfected host cell of claim 8 in which the host cell is prokaryotic.

10. The transformed or transfected host cell of claim 8 in which the host cell is eukaryotic.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 6
        ( D ) OTHER INFORMATION: /label= Xaa
            / note= "Xaa = Ser or Asn"

( x i ) SEQUENCE DESCRIPTION: SEQ ID NO:1:

Asp  Tyr  Ile  Asn  Ala  Xaa
    1                         5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3
        ( D ) OTHER INFORMATION: /label= Xaa
            / note= "Xaa = Any amino acid"

( i x ) FEATURE:
        ( A ) NAME/KEY: Modified-site
        ( B ) LOCATION: 4
        ( D ) OTHER INFORMATION: /label= Xaa
            / note= "Xaa = Any amino acid"

( x i ) SEQUENCE DESCRIPTION: SEQ ID NO:2:

Lys  Cys  Xaa  Xaa  Tyr  Trp  Pro
    1                         5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label= Xaa
            / note= "Xaa = Asp or Asn"

( i x ) FEATURE:
        ( A ) NAME/KEY: Modified-site
        ( B ) LOCATION: 6
        ( D ) OTHER INFORMATION: /label= Xaa
            / note= "Xaa = Ser or Asn"

( x i ) SEQUENCE DESCRIPTION: SEQ ID NO:3:

```
Xaa Tyr Ile Asn Ala Xaa
1               5
```

( 2 ) INFORMATION FOR SEQ ID NO:4:

( i ) SEQUENCE CHARACTERISTICS:
        ( A ) LENGTH: 2790 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 130..1911

( x i ) SEQUENCE DESCRIPTION: SEQ ID NO:4:

```
GGCACGAGCG GCTGGCTCTG CCCGCGTCCG GTCCCGAGCG GGCCTCCCTC GGGCCAGCCC        60

GATGTGACCG AGCCCAGCGG AGCCTGAGCA AGGAGCGGGT CCGTCGCGGA GCCGGAGGGC       120

GGGAGGAAC ATG ACA TCG CGG AGA TGG TTT CAC CCA AAT ATC ACT GGT          168
          Met Thr Ser Arg Arg Trp Phe His Pro Asn Ile Thr Gly
            1               5                  10

GTG GAG GCA GAA AAC CTA CTG TTG ACA AGA GGA GTT GAT GGC AGT TTT        216
Val Glu Ala Glu Asn Leu Leu Leu Thr Arg Gly Val Asp Gly Ser Phe
         15              20                  25

TTG GCA AGG CCT AGT AAA AGT AAC CCT GGA GAC TTC ACA CTT TCC GTT        264
Leu Ala Arg Pro Ser Lys Ser Asn Pro Gly Asp Phe Thr Leu Ser Val
 30              35                  40                      45

AGA AGA AAT GGA GCT GTC ACC CAC ATC AAG ATT CAG AAC ACT GGT GAT        312
Arg Arg Asn Gly Ala Val Thr His Ile Lys Ile Gln Asn Thr Gly Asp
                 50                  55                  60

TAC TAT GAC CTG TAT GGA GGG GAG AAA TTT GCC ACT TTG GCT GAG TTG        360
Tyr Tyr Asp Leu Tyr Gly Gly Glu Lys Phe Ala Thr Leu Ala Glu Leu
                 65                  70                  75

GTC CAG TAT TAC ATG GAA CAT CAC GGG CAA TTA AAA GAG AAG AAT GGA        408
Val Gln Tyr Tyr Met Glu His His Gly Gln Leu Lys Glu Lys Asn Gly
             80                  85                  90

GAT GTC ATT GAG CTT AAA TAT CCT CTG AAC TGT GCA GAT CCT ACC TCT        456
Asp Val Ile Glu Leu Lys Tyr Pro Leu Asn Cys Ala Asp Pro Thr Ser
         95                 100                 105

GAA AGG TGG TTT CAT GGA CAT CTC TCT GGG AAA GAA GCA GAG AAA TTA        504
Glu Arg Trp Phe His Gly His Leu Ser Gly Lys Glu Ala Glu Lys Leu
110                 115                 120                 125

TTA ACT GAA AAA GGA AAA CAT GGT AGT TTT CTT GTA CGA GAG AGC CAG        552
Leu Thr Glu Lys Gly Lys His Gly Ser Phe Leu Val Arg Glu Ser Gln
                130                 135                 140

AGC CAC CCT GGA GAT TTT GTT CTT TCT GTG CGC ACT GGT GAT GAC AAA        600
Ser His Pro Gly Asp Phe Val Leu Ser Val Arg Thr Gly Asp Asp Lys
                145                 150                 155

GGG GAG AGC AAT GAC GGC AAG TCT AAA GTG ACC CAT GTT ATG ATT CGC        648
Gly Glu Ser Asn Asp Gly Lys Ser Lys Val Thr His Val Met Ile Arg
            160                 165                 170

TGT CAG GAA CTG AAA TAC GAC GTT GGT GGA GGA GAA CGG TTT GAT TCT        696
Cys Gln Glu Leu Lys Tyr Asp Val Gly Gly Gly Glu Arg Phe Asp Ser
        175                 180                 185

TTG ACA GAT CTT GTG GAA CAT TAT AAG AAG AAT CCT ATG GTG GAA ACA        744
Leu Thr Asp Leu Val Glu His Tyr Lys Lys Asn Pro Met Val Glu Thr
190                 195                 200                 205

TTG GGT ACA GTA CTA CAA CTC AAG CAG CCC CAA TTC TCG ACT CGT ATA        792
Leu Gly Thr Val Leu Gln Leu Lys Gln Pro Gln Phe Ser Thr Arg Ile
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 210 |     |     |     |     | 215 |     |     |     |     | 220 |     |      |
| AAT | GCT | GCT | GAA | ATA | GAA | AGC | AGA | GTT | CGA | GAA | CTA | AGC | AAA | TTA | GCT | 840  |
| Asn | Ala | Ala | Glu | Ile | Glu | Ser | Arg | Val | Arg | Glu | Leu | Ser | Lys | Leu | Ala |      |
|     |     |     | 225 |     |     |     |     | 230 |     |     |     |     | 235 |     |     |      |
| GAG | ACC | ACA | GAT | AAA | GTC | AAA | CAA | GGC | TTT | TGG | GAA | GAA | TTT | GAG | ACA | 888  |
| Glu | Thr | Thr | Asp | Lys | Val | Lys | Gln | Gly | Phe | Trp | Glu | Glu | Phe | Glu | Thr |      |
|     |     | 240 |     |     |     |     | 245 |     |     |     |     | 250 |     |     |     |      |
| CTA | CAA | CAA | CAG | GAG | TGC | AAA | CTT | CTC | TAC | AGC | CGA | AAA | GAG | GGT | CAA | 936  |
| Leu | Gln | Gln | Gln | Glu | Cys | Lys | Leu | Leu | Tyr | Ser | Arg | Lys | Glu | Gly | Gln |      |
|     | 255 |     |     |     |     | 260 |     |     |     |     | 265 |     |     |     |     |      |
| AGG | CAA | GAA | AAC | AAA | AAC | AAA | AAT | AGA | TAT | AAA | AAC | ATC | CTG | CCC | TTT | 984  |
| Arg | Gln | Glu | Asn | Lys | Asn | Lys | Asn | Arg | Tyr | Lys | Asn | Ile | Leu | Pro | Phe |      |
| 270 |     |     |     |     | 275 |     |     |     |     | 280 |     |     |     |     | 285 |      |
| GAT | CAT | ACC | AGG | GTT | GTC | CTC | ACG | ATC | TGT | GAT | CCC | AAT | GAG | CCT | GTT | 1032 |
| Asp | His | Thr | Arg | Val | Val | Leu | Thr | Ile | Cys | Asp | Pro | Asn | Glu | Pro | Val |      |
|     |     |     |     | 290 |     |     |     |     | 295 |     |     |     |     | 300 |     |      |
| TCA | GAT | TAC | ATC | AAT | GCA | AAT | ATC | ATC | ATG | CCT | GAA | TTT | GAA | ACC | AAG | 1080 |
| Ser | Asp | Tyr | Ile | Asn | Ala | Asn | Ile | Ile | Met | Pro | Glu | Phe | Glu | Thr | Lys |      |
|     |     |     |     | 305 |     |     |     | 310 |     |     |     |     | 315 |     |     |      |
| TGC | AAC | AAT | TCA | AAG | CCC | AAA | AAG | AGT | TAC | ATT | GCC | ACA | CAA | GGC | TGC | 1128 |
| Cys | Asn | Asn | Ser | Lys | Pro | Lys | Lys | Ser | Tyr | Ile | Ala | Thr | Gln | Gly | Cys |      |
|     |     |     | 320 |     |     |     |     | 325 |     |     |     |     | 330 |     |     |      |
| CTG | CAA | AAC | ACG | GTG | AAT | GAC | TTT | TGG | CGG | ATG | GTG | TTC | CAA | GAA | AAC | 1176 |
| Leu | Gln | Asn | Thr | Val | Asn | Asp | Phe | Trp | Arg | Met | Val | Phe | Gln | Glu | Asn |      |
|     | 335 |     |     |     |     | 340 |     |     |     |     | 345 |     |     |     |     |      |
| TCC | CGA | GTG | ATT | GTC | ATG | ACA | ACG | AAA | GAA | GTG | GAG | AGA | GGA | AAG | AGT | 1224 |
| Ser | Arg | Val | Ile | Val | Met | Thr | Thr | Lys | Glu | Val | Glu | Arg | Gly | Lys | Ser |      |
| 350 |     |     |     |     | 355 |     |     |     |     | 360 |     |     |     |     | 365 |      |
| AAA | TGT | GCT | CAA | TAC | TGG | CCT | GAT | GAG | TAT | GCT | CTA | AAA | GAA | TAT | GGC | 1272 |
| Lys | Cys | Ala | Gln | Tyr | Trp | Pro | Asp | Glu | Tyr | Ala | Leu | Lys | Glu | Tyr | Gly |      |
|     |     |     |     | 370 |     |     |     |     | 375 |     |     |     |     | 380 |     |      |
| GTC | ATG | CGT | GTT | AGG | AAC | GTC | AAA | GAA | AGC | GCC | GCT | CAT | GAC | TAT | ACG | 1320 |
| Val | Met | Arg | Val | Arg | Asn | Val | Lys | Glu | Ser | Ala | Ala | His | Asp | Tyr | Thr |      |
|     |     |     | 385 |     |     |     |     | 390 |     |     |     |     | 395 |     |     |      |
| CTA | AGA | GAA | CTT | AAA | CTT | TCA | AAG | GTT | GGA | CAA | GGG | AAT | ACG | GAG | AGA | 1368 |
| Leu | Arg | Glu | Leu | Lys | Leu | Ser | Lys | Val | Gly | Gln | Gly | Asn | Thr | Glu | Arg |      |
|     |     | 400 |     |     |     |     | 405 |     |     |     |     | 410 |     |     |     |      |
| ACG | GTC | TGG | CAA | TAC | CAC | TTT | CGG | ACC | TGG | CCG | GAC | CAC | GGC | GTG | CCC | 1416 |
| Thr | Val | Trp | Gln | Tyr | His | Phe | Arg | Thr | Trp | Pro | Asp | His | Gly | Val | Pro |      |
|     | 415 |     |     |     |     | 420 |     |     |     |     | 425 |     |     |     |     |      |
| AGC | GAC | CCT | GGG | GGC | GTG | CTG | GAC | TTC | CTG | GAG | GAG | GTG | CAC | CAT | AAG | 1464 |
| Ser | Asp | Pro | Gly | Gly | Val | Leu | Asp | Phe | Leu | Glu | Glu | Val | His | His | Lys |      |
| 430 |     |     |     |     | 435 |     |     |     |     | 440 |     |     |     |     | 445 |      |
| CAG | GAG | AGC | ATC | ATG | GAT | GCA | GGG | CCG | GTC | GTG | GTG | CAC | TGC | AGT | GCT | 1512 |
| Gln | Glu | Ser | Ile | Met | Asp | Ala | Gly | Pro | Val | Val | Val | His | Cys | Ser | Ala |      |
|     |     |     |     | 450 |     |     |     |     | 455 |     |     |     |     | 460 |     |      |
| GGA | ATT | GGC | CGG | ACA | GGG | ACG | TTC | ATT | GTG | ATT | GAT | ATT | CTT | ATT | GAC | 1560 |
| Gly | Ile | Gly | Arg | Thr | Gly | Thr | Phe | Ile | Val | Ile | Asp | Ile | Leu | Ile | Asp |      |
|     |     |     | 465 |     |     |     |     | 470 |     |     |     |     | 475 |     |     |      |
| ATC | ATC | AGA | GAG | AAA | GGT | GTT | GAC | TGC | GAT | ATT | GAC | GTT | CCC | AAA | ACC | 1608 |
| Ile | Ile | Arg | Glu | Lys | Gly | Val | Asp | Cys | Asp | Ile | Asp | Val | Pro | Lys | Thr |      |
|     |     | 480 |     |     |     |     | 485 |     |     |     |     | 490 |     |     |     |      |
| ATC | CAG | ATG | GTG | CGG | TCT | CAG | AGG | TCA | GGG | ATG | GTC | CAG | ACA | GAA | GCA | 1656 |
| Ile | Gln | Met | Val | Arg | Ser | Gln | Arg | Ser | Gly | Met | Val | Gln | Thr | Glu | Ala |      |
|     | 495 |     |     |     |     | 500 |     |     |     |     | 505 |     |     |     |     |      |
| CAG | TAC | CGA | TTT | ATC | TAT | ATG | GCG | GTC | CAG | CAT | TAT | ATT | GAA | ACA | CTA | 1704 |
| Gln | Tyr | Arg | Phe | Ile | Tyr | Met | Ala | Val | Gln | His | Tyr | Ile | Glu | Thr | Leu |      |
| 510 |     |     |     |     | 515 |     |     |     |     | 520 |     |     |     |     | 525 |      |
| CAG | CGC | AGG | ATT | GAA | GAA | GAG | CAG | AAA | AGC | AAG | AGG | AAA | GGG | CAC | GAA | 1752 |
| Gln | Arg | Arg | Ile | Glu | Glu | Glu | Gln | Lys | Ser | Lys | Arg | Lys | Gly | His | Glu |      |

|  |  |  |  |  |  |  |  |  |  |  |  |  |  |  |  |
|---|---|---|---|---|---|---|---|---|---|---|---|---|---|---|---|
|  |  |  | 530 |  |  |  |  | 535 |  |  |  |  | 540 |  |  |
| TAT | ACA | AAT | ATT | AAG | TAT | TCT | CTA | GCG | GAC | CAG | ACG | AGT | GGA | GAT | CAG | 1800 |
| Tyr | Thr | Asn | Ile | Lys | Tyr | Ser | Leu | Ala | Asp | Gln | Thr | Ser | Gly | Asp | Gln |  |
|  |  |  | 545 |  |  |  |  | 550 |  |  |  |  | 555 |  |  |
| AGC | CCT | CTC | CCG | CCT | TGT | ACT | CCT | TCG | CCA | CCC | TGT | GCA | GAA | ATG | AGA | 1848 |
| Ser | Pro | Leu | Pro | Pro | Cys | Thr | Pro | Ser | Pro | Pro | Cys | Ala | Glu | Met | Arg |  |
|  |  | 560 |  |  |  |  | 565 |  |  |  |  | 570 |  |  |  |
| GAA | GAC | AGT | GCT | AGA | GTC | TAT | GAA | AAC | GTG | GGC | CTG | ATG | CAA | CAG | CAG | 1896 |
| Glu | Asp | Ser | Ala | Arg | Val | Tyr | Glu | Asn | Val | Gly | Leu | Met | Gln | Gln | Gln |  |
|  | 575 |  |  |  |  | 580 |  |  |  |  | 585 |  |  |  |  |  |
| AAA | AGT | TTC | AGA | TGAGAAACC | TGCCAAAACT | TCAGCACAGA | AATAGATGTG |  |  |  |  |  |  |  |  | 1948 |
| Lys | Ser | Phe | Arg |  |  |  |  |  |  |  |  |  |  |  |  |  |
| 590 |  |  |  |  |  |  |  |  |  |  |  |  |  |  |  |  |

```
GACTTTCACC TCTCCCTAAA AAGATCAGGA CCAGACGCAA GAAAGTTTAT GTGAAGTCTG    2008

AATTTGGATT TGGAAGGCTT GCAATGTGGT TGACTACCTT TTGATAAGCA AAATTTGAAA    2068

CCATTTAAAG ACCACTGTAT TTTAACTCAA CAATACCTGC TTCCCAATTA CTCATTTCCT    2128

CAGATAAGAA GAAATCATCT CTACAATGTA GACAACATTA TATTTATAG AATTTGTTTG     2188

AAATTGAGGA AGCAGTTAAA TTGTGCGCTG TATTTTGCAG ATTATGGGGA TTCAAATTCT    2248

AGTAATAGGC TTTTTTATTT TTATTTTTAT ACCCTTAACC AGTTTAATTT TTTTTTTTCC    2308

TCATTGTTGG GGATGATGAG AAGAAATGAT TTGGGAAAAT TAAGTAACAA CGACCTAGAA    2368

AAGTGAGAAC AATCTCATTT ACCATCATGT ATCCAGTAGT GGATAATTCA TTTTGATGGC    2428

TTCTATTTTG GCCAAATGAG AATTAAGCCA GTGCCTGAGA CTGTCAGAAG TTGACCTTTG    2488

CACTGGCATT AAAGAGTCAT AGAAAAAGAA TCATGGATAT TTATGAATTA AGGTAAGAGG    2548

TGTGGCTTTT TTTTTTTTCT TTTTTCCAGC CGTTGACCAA TTATAGTTCG GCTGTTGACT    2608

GAGAAGTTGT GGTGGAAACG TTTGCCATAT TTTCTTTGCA TTTGAATAAT TGTCTTGTAC    2668

TTAGAAAAAA GGCGTCTATG AATGACCAGT GTTTTGGTC GCCAAATGTT GCTGACAAAC     2728

TTATCCCAAA ACTTTAGTGG CTTAAAAAAA CCTGCCCCCA ACTGTTAGTC AATTGAGCTG    2788

GG                                                                   2790
```

( 2 ) INFORMATION FOR SEQ ID NO:5:

( i ) SEQUENCE CHARACTERISTICS:
        ( A ) LENGTH: 593 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Thr | Ser | Arg | Arg | Trp | Phe | His | Pro | Asn | Ile | Thr | Gly | Val | Glu | Ala |
|---|---|---|---|---|---|---|---|---|---|---|---|---|---|---|---|
| 1 |  |  |  | 5 |  |  |  |  | 10 |  |  |  |  | 15 |  |
| Glu | Asn | Leu | Leu | Leu | Thr | Arg | Gly | Val | Asp | Gly | Ser | Phe | Leu | Ala | Arg |
|  |  |  | 20 |  |  |  |  | 25 |  |  |  |  | 30 |  |  |
| Pro | Ser | Lys | Ser | Asn | Pro | Gly | Asp | Phe | Thr | Leu | Ser | Val | Arg | Arg | Asn |
|  |  | 35 |  |  |  |  | 40 |  |  |  |  | 45 |  |  |  |
| Gly | Ala | Val | Thr | His | Ile | Lys | Ile | Gln | Asn | Thr | Gly | Asp | Tyr | Tyr | Asp |
|  | 50 |  |  |  |  | 55 |  |  |  |  | 60 |  |  |  |  |
| Leu | Tyr | Gly | Gly | Glu | Lys | Phe | Ala | Thr | Leu | Ala | Glu | Leu | Val | Gln | Tyr |
| 65 |  |  |  |  | 70 |  |  |  |  | 75 |  |  |  |  | 80 |
| Tyr | Met | Glu | His | His | Gly | Gln | Leu | Lys | Glu | Lys | Asn | Gly | Asp | Val | Ile |
|  |  |  |  | 85 |  |  |  |  | 90 |  |  |  |  | 95 |  |
| Glu | Leu | Lys | Tyr | Pro | Leu | Asn | Cys | Ala | Asp | Pro | Thr | Ser | Glu | Arg | Trp |
|  |  |  | 100 |  |  |  |  | 105 |  |  |  |  | 110 |  |  |

| | | | | | | | | | | | | | | |
|---|---|---|---|---|---|---|---|---|---|---|---|---|---|---|
| Phe | His | Gly | His | Leu | Ser | Gly | Lys | Glu | Ala | Glu | Lys | Leu | Leu | Thr | Glu |
| | | 115 | | | | 120 | | | | | 125 | | | | |
| Lys | Gly | Lys | His | Gly | Ser | Phe | Leu | Val | Arg | Glu | Ser | Gln | Ser | His | Pro |
| | 130 | | | | 135 | | | | | 140 | | | | | |
| Gly | Asp | Phe | Val | Leu | Ser | Val | Arg | Thr | Gly | Asp | Asp | Lys | Gly | Glu | Ser |
| 145 | | | | | 150 | | | | | 155 | | | | | 160 |
| Asn | Asp | Gly | Lys | Ser | Lys | Val | Thr | His | Val | Met | Ile | Arg | Cys | Gln | Glu |
| | | | | 165 | | | | | 170 | | | | | 175 | |
| Leu | Lys | Tyr | Asp | Val | Gly | Gly | Gly | Glu | Arg | Phe | Asp | Ser | Leu | Thr | Asp |
| | | | 180 | | | | | 185 | | | | | 190 | | |
| Leu | Val | Glu | His | Tyr | Lys | Lys | Asn | Pro | Met | Val | Glu | Thr | Leu | Gly | Thr |
| | | 195 | | | | | 200 | | | | | 205 | | | |
| Val | Leu | Gln | Leu | Lys | Gln | Pro | Gln | Phe | Ser | Thr | Arg | Ile | Asn | Ala | Ala |
| | 210 | | | | | 215 | | | | | 220 | | | | |
| Glu | Ile | Glu | Ser | Arg | Val | Arg | Glu | Leu | Ser | Lys | Leu | Ala | Glu | Thr | Thr |
| 225 | | | | | 230 | | | | | 235 | | | | | 240 |
| Asp | Lys | Val | Lys | Gln | Gly | Phe | Trp | Glu | Glu | Phe | Glu | Thr | Leu | Gln | Gln |
| | | | | 245 | | | | | 250 | | | | | 255 | |
| Gln | Glu | Cys | Lys | Leu | Leu | Tyr | Ser | Arg | Lys | Glu | Gly | Gln | Arg | Gln | Glu |
| | | | 260 | | | | | 265 | | | | | 270 | | |
| Asn | Lys | Asn | Lys | Asn | Arg | Tyr | Lys | Asn | Ile | Leu | Pro | Phe | Asp | His | Thr |
| | | | 275 | | | | | 280 | | | | | 285 | | |
| Arg | Val | Val | Leu | Thr | Ile | Cys | Asp | Pro | Asn | Glu | Pro | Val | Ser | Asp | Tyr |
| | 290 | | | | | 295 | | | | | 300 | | | | |
| Ile | Asn | Ala | Asn | Ile | Ile | Met | Pro | Glu | Phe | Glu | Thr | Lys | Cys | Asn | Asn |
| 305 | | | | | 310 | | | | | 315 | | | | | 320 |
| Ser | Lys | Pro | Lys | Lys | Ser | Tyr | Ile | Ala | Thr | Gln | Gly | Cys | Leu | Gln | Asn |
| | | | | 325 | | | | | 330 | | | | | 335 | |
| Thr | Val | Asn | Asp | Phe | Trp | Arg | Met | Val | Phe | Gln | Glu | Asn | Ser | Arg | Val |
| | | | 340 | | | | | 345 | | | | | 350 | | |
| Ile | Val | Met | Thr | Thr | Lys | Glu | Val | Glu | Arg | Gly | Lys | Ser | Lys | Cys | Ala |
| | | 355 | | | | | 360 | | | | | 365 | | | |
| Gln | Tyr | Trp | Pro | Asp | Glu | Tyr | Ala | Leu | Lys | Glu | Tyr | Gly | Val | Met | Arg |
| | 370 | | | | | 375 | | | | | 380 | | | | |
| Val | Arg | Asn | Val | Lys | Glu | Ser | Ala | Ala | His | Asp | Tyr | Thr | Leu | Arg | Glu |
| 385 | | | | | 390 | | | | | 395 | | | | | 400 |
| Leu | Lys | Leu | Ser | Lys | Val | Gly | Gln | Gly | Asn | Thr | Glu | Arg | Thr | Val | Trp |
| | | | | 405 | | | | | 410 | | | | | 415 | |
| Gln | Tyr | His | Phe | Arg | Thr | Trp | Pro | Asp | His | Gly | Val | Pro | Ser | Asp | Pro |
| | | | 420 | | | | | 425 | | | | | 430 | | |
| Gly | Gly | Val | Leu | Asp | Phe | Leu | Glu | Glu | Val | His | His | Lys | Gln | Glu | Ser |
| | | 435 | | | | | 440 | | | | | 445 | | | |
| Ile | Met | Asp | Ala | Gly | Pro | Val | Val | Val | His | Cys | Ser | Ala | Gly | Ile | Gly |
| | 450 | | | | | 455 | | | | | 460 | | | | |
| Arg | Thr | Gly | Thr | Phe | Ile | Val | Ile | Asp | Ile | Leu | Ile | Asp | Ile | Ile | Arg |
| 465 | | | | | 470 | | | | | 475 | | | | | 480 |
| Glu | Lys | Gly | Val | Asp | Cys | Asp | Ile | Asp | Val | Pro | Lys | Thr | Ile | Gln | Met |
| | | | | 485 | | | | | 490 | | | | | 495 | |
| Val | Arg | Ser | Gln | Arg | Ser | Gly | Met | Val | Gln | Thr | Glu | Ala | Gln | Tyr | Arg |
| | | | 500 | | | | | 505 | | | | | 510 | | |
| Phe | Ile | Tyr | Met | Ala | Val | Gln | His | Tyr | Ile | Glu | Thr | Leu | Gln | Arg | Arg |
| | | | 515 | | | | | 520 | | | | | 525 | | |
| Ile | Glu | Glu | Glu | Gln | Lys | Ser | Lys | Arg | Lys | Gly | His | Glu | Tyr | Thr | Asn |

|  | 530 |  |  |  | 535 |  |  |  |  | 540 |  |  |  |
|---|---|---|---|---|---|---|---|---|---|---|---|---|---|

Ile Lys Tyr Ser Leu Ala Asp Gln Thr Ser Gly Asp Gln Ser Pro Leu
545                 550                 555                 560

Pro Pro Cys Thr Pro Ser Pro Pro Cys Ala Glu Met Arg Glu Asp Ser
                565                 570                 575

Ala Arg Val Tyr Glu Asn Val Gly Leu Met Gln Gln Gln Lys Ser Phe
                580                 585                 590

Arg ( 2 ) INFORMATION FOR SEQ ID NO:6:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..177

( x i ) SEQUENCE DESCRIPTION: SEQ ID NO:6:

```
AAT ATC ATC ATG CCT GAA TTT GAA ACC AAG TGC AAC AAT TCA AAG CCC        48
Asn Ile Ile Met Pro Glu Phe Glu Thr Lys Cys Asn Asn Ser Lys Pro
 1               5                  10                  15

AAA AAG AGT TAC ATT GCC ACA CAA GGC TGC CTG CAA AAC ACG GTG AAT        96
Lys Lys Ser Tyr Ile Ala Thr Gln Gly Cys Leu Gln Asn Thr Val Asn
            20                  25                  30

GAC TTT TGG CGG ATG GTG TTC CAA GAA AAC TCC CGA GTG ATT GTC ATG       144
Asp Phe Trp Arg Met Val Phe Gln Glu Asn Ser Arg Val Ile Val Met
        35                  40                  45

ACA ACG AAA GAA GTG GAG AGA GGA AAG AGT AAA                           177
Thr Thr Lys Glu Val Glu Arg Gly Lys Ser Lys
    50                  55
```

( 2 ) INFORMATION FOR SEQ ID NO:7:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Asn Ile Ile Met Pro Glu Phe Glu Thr Lys Cys Asn Asn Ser Lys Pro
 1               5                  10                  15

Lys Lys Ser Tyr Ile Ala Thr Gln Gly Cys Leu Gln Asn Thr Val Asn
            20                  25                  30

Asp Phe Trp Arg Met Val Phe Gln Glu Asn Ser Arg Val Ile Val Met
        35                  40                  45

Thr Thr Lys Glu Val Glu Arg Gly Lys Ser Lys
    50                  55

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
      ( A ) NAME/KEY: Modified-site
      ( B ) LOCATION: 1
      ( D ) OTHER INFORMATION: /label= Xaa
            / note= "Xaa = Asp or Glu or Gly"

( i x ) FEATURE:
      ( A ) NAME/KEY: Modified-site
      ( B ) LOCATION: 2
      ( D ) OTHER INFORMATION: /label= Xaa
            / note= "Xaa = Ser or Asn"

( i x ) FEATURE:
      ( A ) NAME/KEY: Modified-site
      ( B ) LOCATION: 3
      ( D ) OTHER INFORMATION: /label= Xaa
            / note= "Xaa = Asx"

( x i ) SEQUENCE DESCRIPTION: SEQ ID NO:8:

Xaa Xaa Xaa Tyr Ile Asn Ala
1               5

( 2 ) INFORMATION FOR SEQ ID NO:9:

( i ) SEQUENCE CHARACTERISTICS:
          ( A ) LENGTH: 27 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:9:

GGAATTCGAN TCNGAYTAYA THAAYGC                                                27

( 2 ) INFORMATION FOR SEQ ID NO:10:

( i ) SEQUENCE CHARACTERISTICS:
          ( A ) LENGTH: 27 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:10:

GGAATTCGAN ARYGAYTAYA THAAYGC                                                27

( 2 ) INFORMATION FOR SEQ ID NO:11:

( i ) SEQUENCE CHARACTERISTICS:
          ( A ) LENGTH: 27 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:11:

GGAATTCGGN TCNRAYTAYA THAAYGC                                                27

( 2 ) INFORMATION FOR SEQ ID NO:12:

( i ) SEQUENCE CHARACTERISTICS:
          ( A ) LENGTH: 7 amino acids
          ( B ) TYPE: amino acid
          ( C ) STRANDEDNESS: unknown
          ( D ) TOPOLOGY: unknown ( i i ) MOLECULE TYPE: peptide ( i x ) FEATURE:
        ( A ) NAME/KEY: Modified-site
        ( B ) LOCATION: 3
        ( D ) OTHER INFORMATION: /label= Xaa
            / note= "Xaa = Ala or Asp"

( i x ) FEATURE:
        ( A ) NAME/KEY: Modified-site
        ( B ) LOCATION: 4
        ( D ) OTHER INFORMATION: /label= Xaa
            / note= "Xaa = Gln or Glu"

( x i ) SEQUENCE DESCRIPTION: SEQ ID NO:12:

Lys Cys Xaa Xaa Tyr Trp Pro
1              5

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 20
        ( D ) OTHER INFORMATION: /label= N
            / note= "N = G, A, T, or C."

( x i ) SEQUENCE DESCRIPTION: SEQ ID NO:13:

CGGGATCCGG CCARTAYTSN GCRCAYTT                                                       28

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

CGGGATCCGG CCARTAYTSR TCRCAYTT                                                       28

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

CTCGAGTTTT TTTTTTTTTT TTT                                                                  23

( 2 ) INFORMATION FOR SEQ ID NO:16:

( i ) SEQUENCE CHARACTERISTICS:
        ( A ) LENGTH: 52 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

TTTCTTGTGC GTGAGAGCCT CAGCCAGCCT GGAGACTTCG TGCTTTCTGT CC          52

( 2 ) INFORMATION FOR SEQ ID NO:17:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:17:

```
Asn Ala Ser Leu Ile Lys Met Glu Glu Ala Gln Arg Ser Tyr Ile Leu
 1               5                   10                  15
Thr Gln Gly
```

( 2 ) INFORMATION FOR SEQ ID NO:18:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:18:

```
Asn Ala Ser Leu Val Asp Ile Glu Glu Ala Gln Arg Ser Tyr Ile Leu
 1               5                   10                  15
Thr Gln Gly
```

( 2 ) INFORMATION FOR SEQ ID NO:19:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:19:

```
Asn Ala Asn Tyr Ile Lys Asn Gln Leu Leu Gly Pro Asp Glu Asn Ala
 1               5                   10                  15
Lys Thr Tyr Ile Ala Ser Gln Gly
                20
```